US008507643B2

(12) United States Patent  (10) Patent No.: US 8,507,643 B2
Gilbeau et al.  (45) Date of Patent: Aug. 13, 2013

(54) COMPOSITION COMPRISING GLYCEROL, PROCESS FOR OBTAINING SAME AND USE THEREOF IN THE MANUFACTURE OF DICHLOROPROPANOL

(75) Inventors: Patrick Gilbeau, Braine-le-comte (BE); Bruno Jestin, Brussels (BE)

(73) Assignee: Solvay S.A., Brussels (BE)

( * ) Notice: Subject to any disclaimer, the term of this patent is extended or adjusted under 35 U.S.C. 154(b) by 60 days.

(21) Appl. No.: 12/935,538

(22) PCT Filed: Mar. 31, 2009

(86) PCT No.: PCT/EP2009/053766
§ 371 (c)(1),
(2), (4) Date: Sep. 29, 2010

(87) PCT Pub. No.: WO2009/121853
PCT Pub. Date: Oct. 8, 2009

(65) Prior Publication Data
US 2011/0028683 A1 Feb. 3, 2011

(30) Foreign Application Priority Data

Apr. 3, 2008 (FR) ..................... 08 52206
Feb. 27, 2009 (FR) ..................... 09 51260

(51) Int. Cl.
*C08G 59/04* (2006.01)
*C08G 59/02* (2006.01)
*C07C 31/34* (2006.01)
*C07D 301/26* (2006.01)

(52) U.S. Cl.
USPC ........... 528/418; 528/397; 528/500; 528/501; 528/502 R; 568/844; 549/514

(58) Field of Classification Search
USPC ..... 528/418, 397, 500, 501, 502 R; 568/844; 549/514
See application file for complete search history.

(56) References Cited

U.S. PATENT DOCUMENTS

| 280,893 | A | 7/1883 | Baujard |
|---|---|---|---|
| 865,727 | A | 9/1907 | Queneau |
| 2,060,715 | A | 11/1936 | Arvin |
| 2,063,891 | A | 12/1936 | Dreyfus |
| 2,144,612 | A | 1/1939 | Britton et al. |
| 2,198,600 | A | 4/1940 | Britton et al. |
| 2,248,635 | A | 7/1941 | Marple et al. |
| 2,319,876 | A | 5/1943 | Moss |
| 2,444,333 | A | 6/1948 | Castan |
| 2,505,735 | A | 4/1950 | Halbedel |
| 2,726,072 | A | 12/1955 | Herman |
| 2,733,195 | A | 1/1956 | Miller |
| 2,811,227 | A | 10/1957 | O'Connor |
| 2,829,124 | A | 4/1958 | Napravnik et al. |
| 2,860,146 | A | 11/1958 | Furman et al. |
| 2,876,217 | A | 3/1959 | Paschall |
| 2,945,004 | A | 7/1960 | Greenlee |
| 2,960,447 | A | 11/1960 | Anderson et al. |
| 3,026,270 | A | 3/1962 | Robinson, Jr. |
| 3,052,612 | A | 9/1962 | Henegar et al. |
| 3,061,615 | A | 10/1962 | Viriot et al. |
| 3,121,727 | A | 2/1964 | Baliker et al. |
| 3,135,705 | A | 6/1964 | Vandenberg |
| 3,158,580 | A | 11/1964 | Vandenberg |
| 3,158,581 | A | 11/1964 | Vandenberg |
| 3,247,227 | A | 4/1966 | White |
| 3,260,059 | A | 7/1966 | Rosenberg et al. |
| 3,341,491 | A | 9/1967 | Robinson et al. |
| 3,355,511 | A | 11/1967 | Schwarzer |
| 3,385,908 | A | 5/1968 | Schwarzer |
| 3,445,197 | A | 5/1969 | Resh et al. |
| 3,457,282 | A | 7/1969 | Polak et al. |
| 3,618,295 | A | 11/1971 | Geiger et al. |
| 3,711,388 | A | 1/1973 | Gritzner |
| 3,766,221 | A | 10/1973 | Becker |
| 3,839,169 | A | 10/1974 | Moyer |
| 3,865,886 | A | 2/1975 | Schindler et al. |
| 3,867,166 | A | 2/1975 | Sullivan |
| 3,879,180 | A | 4/1975 | Hutgens et al. |
| 3,954,581 | A | 5/1976 | Carlin |
| 3,968,178 | A | 7/1976 | Obrecht et al. |
| 4,003,723 | A | 1/1977 | Schafer et al. |
| 4,011,251 | A | 3/1977 | Tjurin et al. |
| 4,024,301 | A | 5/1977 | Witenhafer et al. |
| 4,104,434 | A | 8/1978 | Johnson |
| 4,127,694 | A | 11/1978 | Murphy et al. |
| 4,173,710 | A | 11/1979 | Boulet et al. |
| 4,197,399 | A | 4/1980 | Noel et al. |
| 4,220,529 | A | 9/1980 | Daude-Lagrave |
| 4,240,885 | A | 12/1980 | Suciu et al. |

(Continued)

FOREIGN PATENT DOCUMENTS

BE 422877 A 8/1937
CN 1135533 11/1996

(Continued)

OTHER PUBLICATIONS

RD 436093, Aug. 10, 2000, Akzo Nobel.
Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).
Herman A. Bruson, et al., "Thermal Decomposition of Glyceryl Carbonates," Journal of the American Chemical Society, vol. 74, Apr. 1952 pp. 2100-2101.
Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.

(Continued)

*Primary Examiner* — Duc Truong
(74) *Attorney, Agent, or Firm* — Oblon, Spivak, McClelland, Maier & Neustadt, L.L.P.

(57) ABSTRACT

A composition comprising glycerol and at least one cyclic oligomer of glycerol, a process for obtaining the composition, and its use in the manufacture of dichloropropanol and of derived products such as epichlorohydrin and epoxy resins.

15 Claims, No Drawings

(56) References Cited

U.S. PATENT DOCUMENTS

| | | |
|---|---|---|
| 4,255,470 A | 3/1981 | Cohen et al. |
| 4,294,776 A | 10/1981 | Hardy et al. |
| 4,309,394 A | 1/1982 | Hudson |
| 4,322,367 A | 3/1982 | Silvis |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,560,812 A | 12/1985 | Blytas |
| 4,595,469 A | 6/1986 | Foller |
| 4,599,178 A | 7/1986 | Blytas |
| 4,609,751 A | 9/1986 | Hajjar |
| 4,634,784 A | 1/1987 | Nagato et al. |
| 4,655,879 A | 4/1987 | Brockmann et al. |
| 4,898,644 A | 2/1990 | Van Horn |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,766,270 A | 6/1998 | Neuman et al. |
| 5,779,915 A | 7/1998 | Becker et al. |
| 5,908,946 A | 6/1999 | Stern et al. |
| 5,955,043 A | 9/1999 | Neuman et al. |
| 5,993,974 A | 11/1999 | Fukushima et al. |
| 6,024,829 A | 2/2000 | Easter et al. |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,831,201 B2 | 12/2001 | Katsuura et al. |
| 6,350,888 B1 | 2/2002 | Strebelle et al. |
| 6,350,922 B1 | 2/2002 | Vosejpka et al. |
| 6,428,759 B1 | 8/2002 | Smith et al. |
| 6,521,794 B2 | 2/2003 | Hirota |
| 6,589,497 B2 | 7/2003 | Smith |
| 6,719,957 B2 | 4/2004 | Brady, Jr. et al. |
| 6,740,633 B2 | 5/2004 | Norenberg et al. |
| 6,806,396 B2 | 10/2004 | Gelblum et al. |
| 7,126,032 B1 | 10/2006 | Aiken |
| 7,128,890 B2 | 10/2006 | Ollivier |
| 7,453,008 B2 | 11/2008 | Ko et al. |
| 7,557,253 B2 | 7/2009 | Gilbeau |
| 7,584,629 B2 | 9/2009 | Sohn et al. |
| 7,615,670 B2 | 11/2009 | Gilbeau |
| 8,106,246 B2 | 1/2012 | Krafft et al. |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0251831 A1 | 11/2007 | Kaczur et al. |
| 2007/0293707 A1 | 12/2007 | Wolfert et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0161613 A1 | 7/2008 | Krafft et al. |
| 2008/0194847 A1 | 8/2008 | Krafft et al. |
| 2008/0194849 A1 | 8/2008 | Krafft et al. |
| 2008/0194850 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0131631 A1 | 5/2009 | Krafft et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0032617 A1 | 2/2010 | Gilbeau et al. |
| 2010/0105862 A1 | 4/2010 | Krafft et al. |
| 2010/0105964 A1 | 4/2010 | Krafft et al. |
| 2010/0168379 A1 | 7/2010 | Krafft et al. |
| 2010/0170805 A1 | 7/2010 | Krafft et al. |
| 2010/0179300 A1 | 7/2010 | Boulos et al. |
| 2010/0179302 A1 | 7/2010 | Krafft et al. |
| 2010/0212540 A1 | 8/2010 | Bobet et al. |
| 2010/0294727 A1 | 11/2010 | Gilbeau et al. |
| 2010/0305367 A1 | 12/2010 | Borremans |
| 2010/0311942 A1 | 12/2010 | Gilbeau et al. |
| 2011/0152545 A1 | 6/2011 | Balthasart et al. |
| 2011/0166369 A1 | 7/2011 | Krafft et al. |
| 2011/0237773 A1 | 9/2011 | Gilbeau |
| 2012/0010420 A1 | 1/2012 | Gilbeau et al. |
| 2012/0199493 A1 | 8/2012 | Krafft et al. |
| 2012/0199786 A1 | 8/2012 | Gilbeau |

FOREIGN PATENT DOCUMENTS

| | | |
|---|---|---|
| CN | 1296003 A | 5/2001 |
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 4335311 A1 | 4/1995 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |
| EP | 0563720 A1 | 10/1993 |
| EP | 0568389 A1 | 11/1993 |
| EP | 0582201 A2 | 2/1994 |
| EP | 0 618 170 | 10/1994 |

| | | | | | | |
|---|---|---|---|---|---|---|
| EP | 0 916 624 | 5/1999 | | JP | 62242638 A | 10/1987 |
| EP | 0919551 A1 | 6/1999 | | JP | 63195288 A | 8/1988 |
| EP | 0 774 450 | 2/2000 | | JP | 2-137704 | 5/1990 |
| EP | 0 979 671 | 2/2000 | | JP | 03014527 A | 1/1991 |
| EP | 1059278 A2 | 12/2000 | | JP | 03223267 A | 10/1991 |
| EP | 1106237 A1 | 6/2001 | | JP | 3223267 A | 10/1991 |
| EP | 1153887 A2 | 11/2001 | | JP | 04089440 A | 3/1992 |
| EP | 1163946 A1 | 12/2001 | | JP | 04-217637 | 8/1992 |
| EP | 1231189 A1 | 8/2002 | | JP | 06-009589 | 1/1994 |
| EP | 1298154 A1 | 4/2003 | | JP | 625196 B2 | 4/1994 |
| EP | 1411027 A1 | 4/2004 | | JP | 06184024 A | 7/1994 |
| EP | 1752435 A1 | 2/2007 | | JP | 6321852 A | 11/1994 |
| EP | 1752436 A1 | 2/2007 | | JP | 08-003087 | 1/1996 |
| EP | 1760060 A1 | 3/2007 | | JP | 859593 | 3/1996 |
| EP | 1762556 A1 | 3/2007 | | JP | 09-2999953 | 11/1997 |
| EP | 1770081 A1 | 4/2007 | | JP | 10139700 A | 5/1998 |
| EP | 1772446 A1 | 4/2007 | | JP | 10218810 A | 8/1998 |
| EP | 1775278 A1 | 4/2007 | | JP | 1998218810 A | 8/1998 |
| EP | 2085364 | 8/2009 | | JP | 20000344692 A | 12/2000 |
| FR | 1 056 360 | 2/1954 | | JP | 2001-037469 | 2/2001 |
| FR | 1 306 231 | 10/1961 | | JP | 2001-213827 A | 8/2001 |
| FR | 1 417 388 | 10/1964 | | JP | 2001-261308 | 9/2001 |
| FR | 1 577 792 | 8/1965 | | JP | 2001-1261581 A | 9/2001 |
| FR | 1476073 A | 4/1967 | | JP | 2001-276572 | 10/2001 |
| FR | 2151107 | 4/1973 | | JP | 2002-02033 A2 | 1/2002 |
| FR | 2180138 | 5/1973 | | JP | 20020038195 A | 2/2002 |
| FR | 2 217 372 | 2/1974 | | JP | 20020265986 A | 9/2002 |
| FR | 2565229 A1 | 12/1985 | | JP | 2002-363153 A | 12/2002 |
| FR | 2752242 A1 | 2/1998 | | JP | 2003-89680 A | 3/2003 |
| FR | 2862644 A1 | 5/2005 | | JP | 2003081891 A | 3/2003 |
| FR | 2868419 A1 | 10/2005 | | JP | 2003-183191 | 7/2003 |
| FR | 2869612 A1 | 11/2005 | | JP | 2003-206473 | 7/2003 |
| FR | 2869613 A1 | 11/2005 | | JP | 2004-518102 | 6/2004 |
| FR | 2872504 A1 | 1/2006 | | JP | 2004-216246 | 8/2004 |
| FR | 2881732 A1 | 8/2006 | | JP | 2005007841 A2 | 1/2005 |
| FR | 2885903 A1 | 11/2006 | | JP | 2005097177 A2 | 4/2005 |
| FR | 2 912 743 | 8/2008 | | JP | 2005-513064 | 5/2005 |
| FR | 2913683 | 9/2008 | | JP | 2005-154292 | 6/2005 |
| FR | 2913683 A1 | 9/2008 | | JP | 2007-008898 | 1/2007 |
| FR | 2 917 411 | 12/2008 | | JP | 2009 263338 | 11/2009 |
| FR | 2918058 A1 | 1/2009 | | KR | 900006513 | 11/1987 |
| FR | 2925045 A1 | 6/2009 | | KR | 1019920003099 B1 | 4/1992 |
| FR | 2929611 A1 | 10/2009 | | KR | 10-514819 B1 | 9/2005 |
| FR | 2935699 A1 | 3/2010 | | PL | 136598 | 3/1986 |
| FR | 2935968 A1 | 3/2010 | | PL | 162910 | 1/1994 |
| GB | 14767 A | 1/1914 | | SU | 123153 | 1/1959 |
| GB | 406345 | 8/1932 | | SU | 1125226 | 11/1984 |
| GB | 404938 A | 1/1934 | | SU | 1159716 | 6/1985 |
| GB | 467481 A | 6/1937 | | SU | 1685969 | 10/1991 |
| GB | 541357 A | 11/1941 | | WO | WO 95/14635 | 6/1995 |
| GB | 724222 | 6/1952 | | WO | WO 95/14639 | 6/1995 |
| GB | 679536 A | 9/1952 | | WO | WO 96/15980 | 5/1996 |
| GB | 702143 A | 1/1954 | | WO | WO 97/48667 | 12/1997 |
| GB | 758665 | 10/1954 | | WO | WO 96/07617 | 3/1998 |
| GB | 736641 A | 9/1955 | | WO | WO 98/37024 | 8/1998 |
| GB | 799567 A | 8/1958 | | WO | WO 99/14208 | 3/1999 |
| GB | 984446 A | 2/1965 | | WO | WO 9932397 A1 | 7/1999 |
| GB | 984633 A | 3/1965 | | WO | WO 0024674 A1 | 5/2000 |
| GB | 1046521 A | 10/1966 | | WO | WO 01/43762 | 6/2001 |
| GB | 1083594 A | 9/1967 | | WO | WO 0141919 A1 | 6/2001 |
| GB | 1286893 A | 8/1972 | | WO | WO 0186220 A2 | 11/2001 |
| GB | 1387668 A | 3/1975 | | WO | WO 02/26672 | 4/2002 |
| GB | 1414976 A | 11/1975 | | WO | WO 02/059536 | 8/2002 |
| GB | 1 493 538 | 4/1976 | | WO | WO 03/064357 | 8/2003 |
| GB | 2173496 A | 10/1986 | | WO | WO 2004/056758 | 7/2004 |
| GB | 2336584 A | 10/1999 | | WO | WO 2005021476 A1 | 3/2005 |
| HU | 2002-003023 | 3/2004 | | WO | WO 20050554167 A1 | 6/2005 |
| JP | 3927230 B2 | 11/1939 | | WO | WO 2005/097722 | 10/2005 |
| JP | 50-062909 | 5/1975 | | WO | WO 2005/115954 | 12/2005 |
| JP | 51021635 B | 7/1976 | | WO | WO 2005/116004 | 12/2005 |
| JP | 55041858 A | 3/1980 | | WO | WO 20060020234 A1 | 2/2006 |
| JP | 5629572 | 3/1981 | | WO | WO 2006/100311 A2 | 9/2006 |
| JP | 5699432 | 8/1981 | | WO | WO 2006/100312 A2 | 9/2006 |
| JP | 56-155009 | 12/1981 | | WO | WO 2006/100313 A2 | 9/2006 |
| JP | 60-258171 | 12/1985 | | WO | WO 2006/100314 A1 | 9/2006 |
| JP | 61-044833 | 3/1986 | | WO | WO 2006/100315 A2 | 9/2006 |
| JP | 61 112066 A | 5/1986 | | WO | WO 2006/100316 A1 | 9/2006 |
| JP | 61-140532 | 6/1986 | | WO | WO 2006/100317 A1 | 9/2006 |
| JP | 61236749 A | 10/1986 | | WO | WO 2006/100318 A2 | 9/2006 |

| | | |
|---|---|---|
| WO | WO 2006/100319 A1 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 A2 | 5/2007 |
| WO | WO2007/144335 | 12/2007 |
| WO | WO 2008/101866 | 8/2008 |
| WO | WO2008/107468 | 9/2008 |
| WO | WO 2008/110588 | 9/2008 |
| WO | WO2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO2009/000773 | 12/2008 |
| WO | WO 2009/016149 A2 | 2/2009 |
| WO | WO 2009026212 A1 | 2/2009 |
| WO | W02009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/121853 | 10/2009 |
| WO | WO2009/121853 A1 | 10/2009 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/066660 | 6/2010 |
| WO | WO 2011/054769 | 5/2011 |
| WO | WO 2011/054770 | 5/2011 |
| WO | WO 2012/016872 | 2/2012 |
| WO | WO 2012/025468 | 3/2012 |

OTHER PUBLICATIONS

Ullmann's Encyclopedia of Industrial Chemistry 5th Ed., vol. A13, 1989, p. 289.

Ullmann's Encyclopedia of Industrial Chemistry 5th Ed., vol. A11, 1988, pp. 354-360.

Attached Application No. FR 06.05325 filed Jun. 14, 2006 by Solvay S.A.-priority document to EP2007/55742 published as WO 2007/144335 (attached herein) 17 pgs.

Attached Application No. FR 07.53863 filed Mar. 15, 2007 by Solvay S.A. and published as FR2913683, 19 pgs (attached herein)-priority document to EP2007/55742 published as WO2007/144335 29 pgs (attached herein).

Gibson, "The preparation, properties, and uses of glycerol derivatives, Part III. The Chlorohydrins", 1931, Chemistry and Industry, Chemical Society, pp. 949-975.

Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.

Fauconner, 1888, "Preparation de l'epichlorhydrine", Bull. Soc. Chim. FR, No. 50, pp. 212-214 (with enclosed translation in English).

Ullmann's Encyclopedia of Industrial Chemistry, "Industrially important epoxides", 1987, Fifth Completely Revised Edition, vol. A9, pp. 539-540.

Bonner et al, "The composition of constant boiling hydrochloric acid at pressures of 50 to 1220 millimeters", 1930, Journal of American Chemical Society, vol. 52, pp. 633-635.

Muskof et al, "Epoxy Resins" in Ullmann's Encyclopedia of Industrial Chemistry, 1987, 5th Ed., vol. A9, pp. 547-563.

Novelli, A., "The preparation of mono-and dichlorohydrins of glycerol", 1930, Anales Farmacia Bioquimica, vol. 1, pp. 8-19 (with English abstract).

Derwent Publications, AN 109:6092 CA, JP 62-242638, Oct. 23, 1987, 1 pg.

Derwent Publications, AN 1987-338139 [48], JP 62-242638, Oct. 23, 1987, 1 pg.

I. Miyakawa et al, Nagoya Sangyo Kagaku Kenkyusho Kenkyu Hokoku, 10, 49-52 (1957). (Abstract in English only). 1 pg.

Han Xiu-Ying et al, Shanxi Daxue Xuebao Bianjibu, 2002, 25(4), 379-80. (Abstract in English only), 1 pg.

Semendyaeva et al, 1981. Khimicheskaya Promyshlennost, Seriya: Khomaya Promyshlennost, 5. 21-2 (CA Summary). XP 002465275, 1 pg.

Rudnenko, EV, et al., 1988, Lakokrasochnye Materially i 1kh Primenenie, 4 69-71 (CA Summary) XP 002465276, 1 pg.

Kirk-Othmer Encyclopedia of Chemical Technology, 1978, 3rd Ed., vol. 4, Blood, Coagulants and Anticoagulants to Cardiovascular Agents. p. 847-848.

Jeffrey Lutje Spelberg, et al, A Tandem Enzyme Reaction to Produce Optically Active Halohydrins, Epoxides and Diols, Tetrahedron: Asymmetry, Elsevier Science Publishers, vol. 10, No. 15, 1999, pp. 2863-2870.

Oleoline.com. Glycerine Market report, Sep. 10, 2003, No. 62, 31 pgs.

Notification Under Act. No. 100/2001, Coll. As Amended by Act No. 93/2004, Coll. to the extent of Annex No. 4 (SPOLEK) Nov. 30, 2004, 80 pgs.

Documentation Under Act. No. 100/2001 Coll. As Amended by Act. No. 93/2004 Coll in the scope of appendix No. 4 (SPOLEK) Jan. 11, 2005, 86 pgs.

K. Weissermel & H.J. Arpe, Industrial Organic Chemistry, Third, Completely Revised Edition, VCH, 1997, pp. 149 & 275.

Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.

Kirk Othmer Encyclopedia of Chemical Technology, Fourth Edition, 1992, vol. 2, p. 156, John Wiley & Sons, Inc.

Ullmann's Encyclopedia of Industrial Chemistry, Fifth, Completely Revised Edition, 1988, vol. A13, pp. 292-293.

The Merck Index, Eleventh Edition, 1989, pp. 759-760.

Ullmann's Encyclopedia of Industrial Chemistry, Fifth completely Revised Edition, vol. A1, 1985, pp. 427-429.

Ullmann's Encyclopedia of Industrial Chemistry, Fifth Completely Revised Edition, vol. A6, 1986, pp. 240-252.

Hancock, E.G., Propylene and its Industrial Derivatives, 1973, pp. 298-332.

K. Weissermel & H.J. Arpe, Industrial Organic Chemistry, Third, Completely Revised Edition, VCH 1997, pp. 149-163.

K. Weissermel & H.J. Arpe, in Industrial Organic Chemistry, Third, Completely Revised Edition, VCH 1997, pp. 275-276.

Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).

Perry's Chemical Engineers' Handbook, Sixth Edition, Robert H. Perry, Don Green, 1984, Section 21-64 to 21-68.

Iwanami et al, Dictionary of Physics and Chemistry, Third Edition, Ryo Midorikawa /Iwanami Shoten, Publishers, May 29, 1971, pp. 270-271, 595 and 726.

Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.

Kirk Othmer Encyclopedia of Chemical Technology, Third Edition, vol. 12, 1980, pp. 1002-1005.

Chemical Engineering Handbook, the 6th Edition, Edited by the Society of Chemical Engineers, published by Maruzen Co, Ltd., 1999, pp. 1296-1306 Pub. Feb. 23, 1999 w/English translation of p. 1296, Table 28.4, p. 1298, left column, lines 4-13 and p. 1305, Table 28.10.

Product Brochure of De Dietrich Company, Apr. 1996, pp. 3, 8 and 9 w/English translation of p. 8, left column, lines 1-4, p. 9.

The Journal of the American Chemical Society, vol. XLV, Jul.-Dec. 1923, pp. 2771-2772.

Berichte Der Deutschen Chemischen Gesellschaft, 1891, vol. 24, pp. 508-510.

Catalogue of Nittetu Chemical Engineering Ltd. (Published in Mar. 1994).

12093 Chemicals, The Chemical Daily Co., Ltd. (Published on Jan. 22, 1993) with attached English translation of relevant excerpts, 24 pgs.

Chemicals Guide, Chemical Daily Co., Ltd. (Published on Jun. 15, 1990) with attached English translation of relevant excerpts.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2006: URL:http://www.unep.or.ip/letc/Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; A review" Michochemical Journal, vol. 85, No. 2, 2007 pp. 183-193; available online Aug. 17, 2006; 12 pp.
Ma Zengxin et al, "recovery of Polyglycerol from residues of Synthetic Glycerol" Riyong Huaxue Gongye, 1997, 4, 21023 (English Abstract only).
Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.
Production and Prospect of the World Natural Glycerol by Zhu Shiyong, Cereals and Oils, vol. 1997, pp. 33-38 (No English Translation).
Vinnolit; Vinnolit receives EU grant for water recycling project: Press Release, 2008: http://www.vinnolit.de/vinnolit.nsf/id/EN_Vinnolit_receives_EU_grant_for_water_recycling_project_.
N.W. Ziels, Journal of American Oil Chemists' Society, Nov. 1956, vol. 33, pp. 556-565.
Perry's Chemical Engineers Handbook, Sixth Edition, McGrew Hill Inc., (1984) Section 18.
Vol. B3: Unit Operations II of Ullmann's Encyclopedia of Industrial Chemistry, Fifth Completely Revised Edition, Published by VCH, 1988.
W. Giger et al., "14C/12C-Ratios in Organic Matter and Hydrocarbons Extracted from Dated Lake Sediments," Nuclear Instruments and Methods in Physics Research B5 (1984), 394-397, XP-002631954.
Jurgen O. Metzger, "Fats and Oils as Renewable Feedstock for Chemistry," Eur. J. Lipid Sci. Technol. (2009), 111, 865-876. XP-002631953.
Bruce M. Bell, "Glycerin as a Renewable Feedstock for Epichlorohydrin Production, The GTE Process," Clean-Soil, Air, Water, vol. 36, No. 6, (2008) pp. 657-661, XP-002631952.
Horsley, Lee H.—"Azeotropic Data-III", The Dow Chemical Co., Midland, MI, American Chemical Society 1973; pp. 1-4; 4 pgs.
Suzawa, Yoshikazu, et al—"Incineration System for Waste Liquid Containing Chlorinated Organic Compounds", Chemical Apparatuses, 1981, vol. 23, No. 11; 34 pgs; Translation in English provided.
D'Alonzo, R.P., et al—"Glyceride Composition of Processed Fats and Oils as Determined by Glass Capillary Gas Chromatography", Journal of American Oil Chemists' Society, 1982, vol. 59, No. 7, pp. 292-295; 4 pgs.
Chemical Engineering Handbook, $6^{th}$ Revised Edition, 2001, pp. 1-36; 56 pgs; Translation in English provided.
"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue n°2, pp. 32-37, published Dec. 31, 1981; 17 pgs; Translation in English provided.
Chengxin, Ren, et al—"Analysis on the Composition of the Byproduct During the Manufacturing Process of S-Epichlorohydrin by GC-MS", Chemical Analysis and Meterage, 2003, vol. 12, Issue No. 3, pp. 25-26; 6 pgs; Translation in English provided.
Encyclopedia of Chemical Technology, vol. 5, Nov. 1993; 6 pgs; Translation in English provided.
"Manufacture and use of epoxy resin", edited by Shanghai Resin Factory, published by China Petrochemical Press, First Edition, Oct. 1974; 16 pgs; Translation in English provided.
Gilman, Henry, et al—"Organic synthesis", Part 1, published by Scientific Publishing, 1957 (with abstract); 4 pgs.
Handbook of Chemical Products, Heavy Organic Chemicals, Second edition, published by Chemical Industry Press, Jan. 1995; 13 pgs; Translation in English provided.
Kiseleva, R. A., et al—"Study of the Interaction of Dibasic Acids with Glycerol", J. App. Chem. USSR, 1971, vol. 44, pp. 2086-2090; 5 pgs.
Handbook of Corrosion Data and Material Selection, published by Chemical Industry Press, edited by Jingyi Zuo, Yu Zuo; First edition, Oct. 1995, 5 pgs; Translation in English provided.
Handbook of Azeotropic Mixture, edited by Information Department of Comprehensive Scientific Technology Research Institution of Fushun City, 1993; 8 pgs; Translation in English provided.
"Industry Chemical Reaction and Application", published by Chinese Scientific Technology University Press, 1999; 4 pgs; Translation in English provided.
"Epoxy resin", published by Shanghai People's Publishing House, 1971; Translation in English provided; 21 pgs.
Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.
Encyclopedia for Chinese Adult Education, 1994, p. 623; 10 pgs; Translation in English provided.
Medium and Long-term Opportunities and Risks of the Biotechnological Production of Bulk Chemicals from renewable Resources—The Potential of White Technology—The BREW project—Final Report—prepared under the European Commission GRXTH Programme (DG Research) Ulrecht, Sep. 2006 (pp. 29-31).
Ullmann's Encyclopedia Industrial Chemistry, $5^{th}$ Ed. vol. A6 (1988) pp. 401-477.
Polymer Science Dictionary, M.S.M., Elsevier Applied Chemistry, London & New York, 1989 p. 86.
Perry's Chemical Engineers' Handbook, $6^{th}$ Edition, Section 21, pp. 21-55.
M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V;—2005 p. 81/-8/5., vol. 5.
Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997. p. 347-355.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 60/734,636, filed Nov. 8, 2005.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
[Unknown Author], Kirk Othmer Encyclopedia of Chemical Technology—vol. 2, p. 156, John Wiley and Sons, 1992.
[Unknown Author]—New Experimental Chemical Course 1, Basic Operation I, Section 4, Separation and Purification, pp. 251-252 (issued on Sep. 20, 1975) with English translation from Shiga International Patent Office, 3 pgs.
March, Jerry—"Reactions, Mechanisms & Structure", Advanced Organic Chemistry, 4th Ed., 1992, pp. 889, 908 and 937; 5 pgs.
[Unknown Author]—Bulletin de la SociétéChimique de Paris—"Analyse des Travaux de Chimie Pure et Appliquée", G. Masson, Editor, Paris, Jul. 4, 1873, Novelle Série, Tome XIX, pp. 97-99; 4 pgs ; comments regarding Friedel & Silva's work on middle of p. 98.
Neuberg, Irene Stephanie—"A New Way of Preparing Glyceraldehyde from Glycerol", Kaiser Wilhelm Institute in Berlin for Biochemi-Dahlem, 1930; 3 pgs; Includes abstract in English.
Krausz, Francois—'Recherches sur les Aldehydes Substitues en α en β. α and β Substituted Aldehydes', University Strasbourg, France ; Ann Chim 12, Nov.-Dec. 1949, 4, pp. 811-831, 23 pgs ; Includes abstract in English.
[Unknown Author]—"Glycerine—An Overview"—by The Soap and Detergent Association, Glycerine and Oleochemical Division, 1990; 27 pgs.
[Unknown Author]—"Commercial Synthesis of Glycerol Begins a New Shell Chemical Corp Plant—A staff Report"; Chemical & Engineering News, 1948, vol. 26, No. 38, pp. 2770-2771; 2 pgs.
Fairbourne, Arthur, et al—"The Partial Esterification of Polyhydric Alcohols . Part XII . The Funstion of Ethylene-oxide Rings", J. Chem. Soc. 1932, republished 1965, pp. 1965-1972; 8 pgs.
Clarke, H.T., et al —"Epichlorohydrin", Organic Syntheses, Coll. vol. 1, pp. 233 (1941) ; vol. 3, p. 47 (1923); 2 pgs.
Braun, Geza—"Epichlorohydrin and Epibromohydrin", Organic Syntheses, Coll. vol. 2, p. 256 (1943) ; vol. 16, p. 30 (1936); 2 pgs.
Conant, J.B., et al—"Glycerol a,y-Dichlorohydrin", Organic Syntheses, Coll. vol. 1, p. 292 (1941); vol. 2, p. 29 (1922); 3 pgs.
Chavanne, G.—"Memoires Presentes a La Societe Chimique", English translation—"Reports Submitted to Chemical Firm", Bull. Soc. Chim. Fr. 1943, 1, EP 06 121 086; 16 pgs.
Schroder, Angela, et al—"Glycerol as a by-product of biodiesel production in Diets for ruminants", 1999, The Regional Institute, Institute of Animal Nutrition, Physiology and Metabolism, University of Kiel, Germany, 6 pgs.
[Unknown Author]—"Chemical Properties and Derivatives of Glycerol ", 1965, Glycerine Producer's Association, $1^{st}$ Edition, 23 pgs.
Busby, G.W., et al—"The Purification of Glycerin by Ion-Exchange", The Journal of the American Oil Chemists' Society, 1952, 3 pgs.

Lamborn, Leebert Lloyd—"Modern Soaps, Candles and Glycerin", $3^{rd}$ Edition, 1918, D. Van Nostrand Company, London, 12 pgs.
Knothe, Gerhard—"Historical perspectives on vegetable oil-based diesel fuels", Industrial Oils, 2001, vol. 12, pp. 1103-1107; 5 pgs.
Schuchardt, Ulf, et al—"Transesterification of Vegetable Oils: A Review", 1998, Braz. Chem Soc., vol. 9, No. 1, pp. 199-210; 12 pgs.
Claude, Sylvain—"Research of new outlets of glycerol-recent developments in France"—1999, Fett/Lipid, No. 3, Wiley-VCH Verlag GmbH, Weinheim, pp. 101-104; 4 pgs.
Prakash, Chandra B.—"A Critical Review of Biodiesel as a Transportation Fuel in Canada", 1998, GCSI—Global Change Strategies International Inc.; 119 pgs.
Fukuda, Hideki, et al—"Review—Biodiesel Fuel Production by Transesterification of Oils", 2001, Journal of Bioscience and Bioengineering; vol. 92, No. 5, pp. 405-416; 12 pgs.
Yong, K.C., et al—"Refining of Crude Glycerine Recovered From Glycerol Residue by Simple Vacuum Distillation", Dec. 2001, Journal of Oil Palm Research, vol. 13, No. 2, pp. 39-44, 6 pgs.
Encyclopedia of Experimental Chemistry I, Basic Operation I, edited by The Chemical Society of Japan, Maruzen Co., Ltd., Nov. 5, 1990, 4th Edition, pp. 161 to 165 and 184 to 191 (no English translation available.
Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312 and 313 (no English translation available).
Clarke et al., Org Synth., Coll. vol. 1, p. 233-234, 1964.
Braun, Org. Synth., Coll., vol. 2, p. 256-259, 1957.
Kirk Othmer Encyclopedia of Chemical Technology, 3rd Edition, vol. 9, pp. 267-289, 1980.
Wu, Guoying, et al., "Preparation of Biodiesel and Glycerol by Methyl Esterification of Cottonseed Oil," China Oil and Fat, (2003), vol. 28, Iss. 4, 70-73, pp. 1-9.
Zhu Shiyong, "Production and Prospects of the World's Natural Glycerin," Cereals and Oils, (1997), Issue 01, 33-38, paetgs 1-15.
Arthur J. Hill et al, "A Synthesis of Beta-Chloro-Ally Chloride," Journal American Chemical Society, 1922, 44(11), 2582-2595.
Physical and Chemical Dictionary (5th Edition), Feb. 20, 1998 (with attached English translation of cited excerpt).
Encyclopaedia CHIMICA, No. 8, $1^{st}$ Edition, Feb. 28, 1962 1-1, (with attached English translation of cited excerpt).
Encyclopaedia CHIMICA, No. 2, $1^{st}$ Edition, Jun. 30, 1960, 1-2, (with attached English translation of cited excerpt).
Klaus Gottlieb, et al., "Glycerine—A Sustainable Raw Material," Chem. Ing. Tech. 66 (1994) Nr.1, S, 64-66 (with attached English translation).
Wissenschaft & Technik, Mar. 1995, pp. 139-142 (no translation).
Milchert et al., "Dehydrochlorination of Glycerol Dichlorohydrin to Epichlorohydrin," *Chem. Papers*, 49 (3) 133-136 (1995).
M. Demarquay, "De La Glycerine," Librairie de la Faculté de Médecine, Paris 1863 (no translation).
Trent et al., "Reactive Stripping in a Rotating Packed Bed for the Production of Hypochlorous Acid", *BHR Group*, Conference Series Publication (1999), 38 (Process Intensification for the Chemical Industry), 217-231.
M. Vajda et al., Membrane-Based Extraction Joined With Membrane-Based Stripping in a Circulating Arrangement II. Extraction of Organic Acids, *Chemical Papers*, (2003), 57(1), 3-10.
U.S. Appl. No. 13/623,979, filed Sep. 21, 2012, Gilbeau.
U.S. Appl. No. 13/755,236, filed Jan. 31, 2013, Krafft, et al.
U.S. Appl. No. 13/709,218, filed Dec. 10, 2012, Boulos, et al.
U.S. Appl. No. 13/813,348, filed Jan. 30, 2013, Gilbeau, et al.
Perry's Chemical Engineers Handbook, Sixth Edition, Mc Graw Hill Inc., 1984, Section 14 (pp. 14-1—14-40).
Perry's Chemical Engineers Handbook, Sixth Edition, Mc Graw Hill Inc., 1984, Section 22-32 to 22-37.
U.S. Appl. No. 12/935,538, filed Sep. 29, 2010, Gilbeau, et al.
U.S. Appl. No. 13/818,753, filed Feb. 25, 2013, Gilbeau, et al.

COMPOSITION COMPRISING GLYCEROL, PROCESS FOR OBTAINING SAME AND USE THEREOF IN THE MANUFACTURE OF DICHLOROPROPANOL

CROSS-REFERENCE TO RELATED APPLICATIONS

The present patent application is a U.S. national stage application under 35 U.S.C. §371 of International Application No. PCT/EP2009/053766 filed Mar. 31, 2009, which claims the benefit of French patent applications FR 08/52206 filed on Apr. 3, 2008 and FR 09/51260 filed on Feb. 29, 2009, the content of both of these applications being incorporated herein by reference.

The present invention relates to a composition comprising glycerol (1,2,3-propanetriol), to a process for obtaining it and to the use of the composition in the manufacture of dichloropropanol and of derived products such as epichlorohydrin and epoxy resins.

Dichloropropanol, for example, is a reaction intermediate in the manufacture of epichlorohydrin and epoxy resins (Kirk-Othmer Encyclopedia of Chemical Technology, Fourth Edition, 1992, Vol. 2, page 156, John Wiley & Sons, Inc.).

According to known processes, dichloropropanol can be obtained in particular by hypochlorination of allyl chloride, by chlorination of allyl alcohol and by hydrochlorination of glycerol. With the latter process, dichloropropanol can be obtained starting from fossil raw materials or renewable raw materials. It is known that petrochemical natural resources, from which the fossil materials originate, for example oil, natural gas or coal, available on Earth are limited.

In some conditions, the hydrochlorination of glycerol starting from renewable raw materials exhibits a selectivity which leaves a lot to be desired, resulting in the formation of some heavy by-products that it is necessary to eliminate.

The invention aims to solve this problem by limiting the formation of heavy by-products and the problems which are related to those heavy by-products.

The invention therefore relates to a composition comprising glycerol and at least one cyclic oligomer of glycerol at a content greater than or equal to 0.01 and less than or equal to 20 g of cyclic oligomer/kg of composition, and to its use in the manufacture of dichloropropanol.

One of the main features of the present invention lies in the low content of cyclic oligomers of glycerol in the glycerol composition used as raw material in the manufacture of dichloropropanol.

Specifically, it has been found that the presence of glycerol oligomers in the glycerol contributes to the formation of heavy by-products in the process for manufacturing dichloropropanol by hydrochlorination of glycerol.

By heavy by-products in the process for manufacturing dichloropropanol by hydrochlorination of glycerol, one intends to denote glycerol oligomers which may be partially chlorinated and/or esterificated.

Without intending to be bound by any theory, it is believed that the composition of such heavy by-products, which is related among others to the chemical structure of the heavy by-products and to their content in the reaction mixture, is important in the process for manufacturing dichloropropanol.

The composition of such heavy by-products is believed to improve the selectivity and the yield of dichloropropanol, starting from glycerol. The heavy by-products in the process for manufacturing dichloropropanol by hydrochlorination of glycerol are believed to behave as a solvent for the hydrochlorination reaction.

However, it is further believed that a too high content in heavy by-products can lead to an increased consumption of the chlorinating agent of glycerol, to a decreased dichloropropanol productivity, to an increase of the viscosity of the reaction medium leading to difficulties of mixing and dissolving the reactants and in particular hydrogen chloride and to an increase in the frequency of the purging operations of the process. It is also further believed, that some partially chlorinated and/or esterificated cyclic oligomers of glycerol have boiling temperature close to the boiling temperature of dichloropropanol which can make separation more difficult and also have a negative impact on down-stream processes using dichloropropanol, like epichlorohydrin and epichlorohydrin derivatives manufacturing processes.

An optimal composition of heavy by-products is necessary. This optimal composition is believed to be controlled by an optimal content of cyclic glycerol oligomers in the glycerol submitted to the hydrochlorination reaction.

In the composition according to the invention, the glycerol content is generally greater than or equal to 500 g of glycerol per kg of composition, usually greater than or equal to 750 g/kg, in many cases greater than or equal to 900 g/kg, commonly greater than or equal to 950 g/kg, often greater than or equal to 990 g/kg, frequently greater than or equal to 999 g/kg, specifically greater than or equal to 999.9 g/kg and in particular greater than or equal to 999.95 g/kg. That glycerol content is usually lower than or equal to 999.99 g/kg of composition.

The expression "cyclic oligomer of glycerol" is understood to mean a cyclic compound resulting from condensation reactions between at least two glycerol molecules, i.e. a compound resulting from condensation reactions between at least two glycerol molecules and the chemical structure of which contains at least one cycle or ring.

In the composition according to the invention, the cyclic oligomer of glycerol is generally a compound resulting from condensation reactions between at least 2 glycerol molecules (dimer), and at most 7 glycerol molecules (heptamer), often at most 6 glycerol molecules (hexamer), frequently at most 4 glycerol molecules (tetramer) and more specifically at most 3 glycerol molecules (trimer).

The cyclic oligomer of glycerol is usually an oligomer of glycerol for which at least some of the carbon atoms are located in the at least one ring of the chemical structure. The number of atoms constituting the ring is generally greater than or equal to 6, often greater than or equal to 7 and sometimes greater than or equal to 8. The number of atoms constituting the ring is generally less than or equal to 20. The ring generally comprises at least two oxygen atoms and often 2 oxygen atoms. Cyclic oligomers of glycerol containing a single ring constituted of 6 atoms, of which 2 of the atoms are oxygen atoms, are particularly suitable. Cyclic oligomers of glycerol containing a single ring constituted of 7 atoms, of which 2 of the atoms are oxygen atoms, are particularly convenient. Cyclic oligomers of glycerol containing a single ring constituted of 8 atoms, of which 2 of the atoms are oxygen atoms, are also particularly suitable.

In the composition according to the invention, the cyclic oligomer of glycerol is preferably chosen from the group consisting of cyclic dimers of glycerol, cyclic trimers of glycerol, cyclic tetramers of glycerol, and mixtures of at least two of these glycerol oligomers.

In the composition according to the invention, the cyclic oligomer of glycerol is often a cyclic compound resulting from condensation reactions between two glycerol molecules, i.e., a cyclic dimer of glycerol.

The dimer of cyclic structure generally comprises at least one ring and often only one ring. The ring generally comprises 6 atoms, often 7 atoms and frequently 8 atoms, of which two atoms are oxygen atoms and the remainder are carbon atoms.

In the composition according to the invention, the cyclic dimer of glycerol usually comprises at least one of the compounds selected from the group consisting of cis- and trans-2,5-bis-(hydroxymethyl)-1,4-dioxane, cis- and trans-2,6-bis (hydroxymethyl)-1,4-dioxane, cis- and trans-6-hydroxy-2-hydroxymethyl-1,4-dioxepane, and cis- and trans-3,7-dihydroxy-1,5-dioxocane, and any mixture of at least two of them.

In the composition according to the invention, the cyclic dimer of glycerol is often a mixture comprising all the preceding isomers.

In the composition according to the invention, the cyclic dimer of glycerol is often a mixture consisting essentially of all the preceding isomers.

In the composition according to the invention, the content of the cyclic oligomer of glycerol is often less than or equal to 10 g of cyclic oligomer/kg of composition, frequently less than or equal to 5 g/kg, commonly less than or equal to 2.5 g/kg, specifically less than or equal to 1 g/kg, more specifically less than or equal to 0.5 g/kg and particularly less than or equal to 0.1 g/kg. This content is often greater than or equal to 0.05 g/kg.

In the composition according to the invention, the content of the cyclic dimer of glycerol is often less than or equal to 10 g of cyclic dimer/kg of composition, frequently less than or equal to 5 g/kg, commonly less than or equal to 2.5 g/kg, specifically less than or equal to 1 g/kg, more specifically less than or equal to 0.5 g/kg and particularly less than or equal to 0.1 g/kg. This content is often greater than or equal to 0.05 g/kg.

In the composition according to the invention, the sum of the contents of cis- and trans-2,5-bis(hydroxymethyl)-1,4-dioxane, cis- and trans-2,6-bis-(hydroxymethyl)-1,4-dioxane, cis- and trans-6-hydroxy-2-hydroxymethyl-1,4-dioxepane, and cis- and trans-3,7-dihydroxy-1,5-dioxocane is often less than or equal to 10 g/kg of composition, frequently less than or equal to 5 g/kg, commonly less than or equal to 2.5 g/kg, specifically less than or equal to 1 g/kg, more specifically less than or equal to 0.5 g/kg and particularly less than or equal to 0.1 g/kg. This content is often greater than or equal to 0.05 g/kg.

The composition according to the invention may in addition contain at least one oligomer of glycerol chosen from the group consisting of oligomers of glycerol of linear structure, of branched structure, and of mixtures of at least two of these oligomers. The additional oligomer of glycerol is often a mixture of at least two of these oligomers.

The expression "oligomers of linear structure" is understood to mean oligomers in which all the carbon atoms are located in one and the same chain of atoms, which is not a ring.

The expression "oligomers of branched structure" is understood to mean oligomers for which the carbon atoms are located in at least two chains of atoms.

The oligomers of glycerol of "linear structure" and the oligomers of glycerol "of branched structure" are not cyclic oligomers of glycerol. They will be referred also further as non cyclic oligomers of glycerol.

In the composition according to the invention, the glycerol oligomer of linear structure and the glycerol oligomer of branched structure are independently preferably chosen from the group consisting of glycerol dimers, glycerol trimers, glycerol tetramers, and mixtures of at least two of these glycerol oligomers.

In the composition according to the invention, the glycerol oligomer of linear structure and the glycerol oligomer of branched structure are independently and frequently a glycerol dimer.

In the composition according to the invention, the glycerol dimer of linear structure and the glycerol dimer of branched structure are often a mixture of the dimer of linear structure, and of at least one dimer of branched structure.

The non cyclic oligomer of glycerol is often a mixture of at least two of the compounds selected from the group consisting of 3-(2,3-dihydroxypropoxy)-propane-1,2-diol (linear oligomer of glycerol), 3-(2-hydroxy-1-hydroxymethylethoxy)propane-1,2-diol (mono branched oligomer of glycerol) and 2-(2-hydroxy-1-hydroxymethylethoxy)propane-1,3-diol (di branched oligomer of glycerol).

In the rest of the document, glycerol oligomers will also be called polyglycerols, and glycerol dimers, trimers, tetramers, etc. will also be called diglycerols, triglycerols, tetraglycerols, etc.

In the composition according to the invention, the non cyclic polyglycerol content is often less than or equal to 10 g/kg of composition, frequently less than or equal to 5 g/kg, specifically less than or equal to 2.5 g/kg, particularly less than or equal to 1 g/kg, more specifically less than or equal to 0.5 g/kg and most particularly less than or equal to 0.1 g/kg. This content is often greater than or equal to 0.05 g/kg.

In the composition according to the invention, the non cyclic diglycerol content is often less than or equal to 10 g/kg of composition, frequently less than or equal to 5 g/kg, commonly less than or equal to 2.5 g/kg, specifically less than or equal to 1 g/kg, more specifically less than or equal to 0.5 g/kg and particularly less than or equal to 0.1 g/kg. This content is often greater than or equal to 0.05 g/kg.

In the composition according to the invention, the content of 3-(2,3-di-hydroxypropoxy)propane-1,2-diol (linear diglycerol) is often less than or equal to 10 g/kg of composition, frequently less than or equal to 5 g/kg, specifically less than or equal to 2.5 g/kg, commonly less than or equal to 1 g/kg, more specifically less than or equal to 0.5 g/kg and particularly less than or equal to 0.1 g/kg. This content is often greater than or equal to 0.05 g/kg.

In the composition according to the invention, the sum of the contents of 3-(2-hydroxy-1-hydroxymethylethoxy)propane-1,2-diol and 2-(2-hydroxy-1-hydroxymethyl-ethoxy)propane-1,3-diol (branched diglycerols) is often less than or equal to 10 g/kg of composition, frequently less than or equal to 5 g/kg, commonly less than or equal to 2.5 g/kg, specifically less than or equal to 1 g/kg, and particularly less than or equal to 0.1 g/kg. This content is often greater than or equal to 0.05 g/kg.

The composition according to the invention generally contains diols as described in Application WO 2009/000773 in the name of SOLVAY SA, from page 1, line 30 to page 2, line 22, the content of which is incorporated here by reference.

The diols are preferably chosen from 1,2-ethanediol (ethylene glycol), 1,2-propanediol (propylene glycol), 1,3-propanediol, 1,2-butanediol, 2,3-butanediol, 1,4-butanediol or a mixture of at least two of these compounds. 1,3-propanediol is particularly preferred.

In the composition according to the invention, the diol content is generally greater than or equal to 0.001 g diol/kg of composition and less than or equal to 100 g diol/kg of composition. This content is often less than or equal to 90 g/kg, commonly less than or equal to 50 g/kg, frequently less than or equal to 10 g/kg, usually less than or equal to 1 g/kg, commonly less than or equal to 0.5 g/kg and frequently less than or equal to 0.2 g/kg. This amount is often greater than or equal to 0.005 g/kg, frequently greater than or equal to 0.01 g/kg, commonly greater than or equal to 0.04 g/kg and usually greater than or equal to 0.1 g/kg.

The composition according to the invention generally contains glycerol alkyl ethers as described in Application WO 2007/144335 in the name of SOLVAY SA, from page 2, line 6 to page 3, line 25, the content of which is incorporated here by reference. Glycerol methyl ethers are particularly suitable.

The oligomers of glycerol are not considered as glycerol alkyl ethers.

The content of glycerol alkyl ethers is generally less than or equal to 90 g/kg of composition, often less than or equal to 50 g/kg, frequently less than or equal to 10 g/kg, commonly less than or equal to 5 g/kg, usually less than or equal to 1 g/kg, more commonly less than or equal to 0.5 g/kg and more frequently less than or equal to 0.2 g/kg. This content is generally greater than or equal to 0.005 g/kg, frequently greater than or equal to 0.01 g/kg, often greater than or equal to 0.04 g/kg and more frequently greater than or equal to 0.1 g/kg.

The composition according to the invention may also comprise monoalcohols, such as the monoalcohols described in Application WO2007/144335 in the name of SOLVAY SA, from page 3, lines 26 to 31, the content of which is incorporated here by reference.

These monoalcohols are generally present at a content greater than or equal to 0.001 g/kg of composition, and often greater than or equal to 0.01 g/kg. This content is generally less than 20 g/kg of product and often less than or equal to 2 g/kg of product.

The composition according to the invention may also comprise water in a content generally greater than or equal to 0.1 g/kg of composition and less than or equal to 200 g/kg. This amount is often less than or equal to 50 g/kg and frequently less than or equal to 20 g/kg.

The composition according to the invention may also comprise at least one fatty acid alkyl ester and/or one glycerol ester and/or one salt as described in Application WO 2007/144335 in the name of SOLVAY SA, from page 5, lines 12 to 20.

These esters are generally present at a content greater than or equal to 0.01 g/kg of composition, often greater than or equal to 1 g/kg and frequently greater than or equal to 5 g/kg. This content is generally less than 50 g/kg of product, and often less than or equal to 30 g/kg, and more often less than or equal to 10 g/kg.

These salts are generally present at a content greater than or equal to 0.0005 g/kg of composition, often greater than or equal to 0.001 g/kg and frequently greater than or equal to 0.01 g/kg. This content is generally less than 10 g/kg, and often less than or equal to 1 g/kg of product, and more often less than or equal to 0.1 g/kg.

The diols, glycerol alkyl ethers, monoalcohols, water, alkyl esters of fatty acids, glycerol esters and salts may be by-products of glycerol manufacturing processes such as, for example, the processes for conversion of oils or fats of plant or animal origin via transesterification, saponification or hydrolysis reactions, processes for conversion of mono- and polysaccharides and derived alcohols, such as fermentation, and thermochemical processes such as hydrogenation and hydrogenolysis.

In the composition according to the invention, the glycerol may have an alkali metal and/or alkaline earth metal content as described in WO 2006/100315 of SOLVAY SA, the content of which is incorporated herein by reference, and especially the passages from page 7, line 11, to page 9, line 10.

In the composition according to the invention, the glycerol may contain elements other than alkali metals and alkaline earth metals as described in WO 2006/100319 of SOLVAY SA, the content of which is incorporated herein by reference, especially the passages from page 2, line 3 to 8, and from page 6, line 20, to page 9, line 14.

In the composition according to the invention, the glycerol may contain an amount of heavy compounds other than glycerol and polyglycerols and whose boiling temperature under a pressure of 1 bar absolute is at least 15° C. greater than the boiling temperature of dichloropropanol as described in WO 2006/100316 of SOLVAY SA the content of which is incorporated herein by reference, especially the passages from page 15, line 32, to page 17, line 33.

In the composition according to the invention, the glycerol may contain nitrogen containing compounds as described in FR 07/59891 of SOLVAY SA the content of which is incorporated herein by reference, especially the passages from page 1, line 28, to page 3, line 20.

The invention also relates to a process for preparing the composition comprising glycerol and at least one cyclic oligomer of glycerol at a content greater than or equal to 0.01 and less than or equal to 20 g of cyclic oligomer/kg of composition, comprising the following steps:
(a) a composition (I) comprising glycerol, of which the content of cyclic oligomer of glycerol is less than 0.01 g/kg of composition, is subjected to a heating operation at a temperature greater than or equal to 25° C. and less than 180° C., in the presence of a basic agent;
(b) the composition (II) obtained at the end of step a) is subjected to a distillation operation or to an evaporation operation, in order to obtain, as a distillate or as an evaporate, a composition comprising glycerol and at least one cyclic oligomer of glycerol at a content greater than or equal to 0.01 g of cyclic oligomer/kg of composition;
(c) optionally, one fraction of the composition (III) obtained at the end of step b) is subjected to at least one purification treatment, so as to obtained a composition comprising glycerol and at least one cyclic oligomer of glycerol at a content of less than or equal to 20 g of cyclic oligomer/kg of composition.

The composition (II) obtained at the end of step a) may optionally be cooled prior to step b).

In the process for manufacturing the composition according to the invention, steps (a) and (b) allows to generate a composition comprising glycerol and at least one cyclic oligomer of glycerol at a content greater than or equal to 0.01 g of cyclic oligomer/kg of composition.

Step (a) may be carried out in any type of reactor, such as for example a plug flow reactor or a stirred reactor.

Step (a) may be carried in continuous mode or in discontinuous mode.

Step (b) may be carried out in any type of distillation columns like for instance, plate columns or packed columns.

Step (b) may be carried out in any type of evaporator like for instance, batch evaporators, thin film evaporators or wiped thin film evaporators.

Step (b) may be carried in continuous mode or in discontinuous mode.

In the process for manufacturing the composition according to the invention, the composition used in step (a) has a content of cyclic oligomer of glycerol often less than or equal to 0.005 g/kg and frequently less than or equal to 0.001 g/kg.

In the process for manufacturing the composition according to the invention, the heating operation of step (a) is carried out at a temperature often greater than 50° C., frequently greater than or equal to 100° C., routinely greater than or equal to 150° C. and specifically greater than or equal to 175° C.

In the process for manufacturing the composition according to the invention, the heating operation of step (a) is carried out under a pressure generally greater than or equal to 0.01 bar absolute, often greater than or equal to 0.5 bar absolute and frequently greater than or equal to 0.2 bar absolute.

In the process for manufacturing the composition according to the invention, the duration of the heating operation of step (a) is generally less than or equal to 8 h, often less than or equal to 6 h and frequently less than or equal to 4 h. This duration is generally greater than or equal to 5 minutes, frequently greater than or equal to 15 minutes, particularly greater than or equal to 60 minutes and specifically greater than or equal to 120 minutes.

In the process for manufacturing the composition according to the invention, the distillation or the evaporation operation of step (b) is carried out at a temperature usually greater than 80° C., frequently greater than or equal to 100° C., routinely greater than or equal to 110° C. and specifically greater than or equal to 130° C. This temperature is generally lower often greater than 250° C., frequently lower than or equal to 200° C., routinely lower than or equal to 190° C. and specifically lower than or equal to 180° C.

In the process for manufacturing the composition according to the invention, the distillation or evaporation operation of step (b) is carried out under a pressure generally greater than or equal to 0.01 mbar absolute, often greater than or equal to 0.1 mbar absolute and frequently greater than or equal to 1 mbar absolute. This pressure is generally lower than or equal to 0.4 bar absolute, often lower than or equal to 60 mbar absolute and frequently lower than or equal to 20 mbar absolute.

In the process for manufacturing the composition according to the invention, the temperature of the optional cooling of composition (II) prior to step (b) is generally less than or equal to 80° C., often less than or equal to 70° C. and more preferably less than or equal to 60° C.

The cooling operation is generally carried out over a duration less than or equal to 60 min, often less than or equal to 30 min, and frequently less than or equal to 15 min.

In the process according to the invention the basic compound of step (a) may be an organic or inorganic basic compound. Organic basic compounds are for example amines, phosphines, ammonium, phosphonium or arsonium hydroxides and alkali and alkaline-earth metal carboxylates. Inorganic basic compounds are preferred. The expression "inorganic compounds" is understood to mean compounds which do not contain a carbon-hydrogen bond. The inorganic basic compound may be chosen from alkali and alkaline-earth metal oxides, hydroxides, carbonates, hydrogen carbonates, phosphates, hydrogen phosphates and borates, and mixtures thereof. Alkali and alkaline-earth metal oxides and hydroxides are preferred. Sodium and calcium hydroxides are preferred and sodium hydroxide is particularly preferred.

In the process according to the invention, the basic compound of step (a) may be in the form of a liquid, an essentially anhydrous solid, a hydrated solid, an aqueous and/or organic solution or an aqueous and/or organic suspension. The basic compound is preferably in the form of an essentially anhydrous solid, a hydrated solid, an aqueous solution or an aqueous suspension. Sodium hydroxide solutions are preferred.

Under these conditions of step (a), the degree of conversion of the glycerol, defined as the ratio between the amount of glycerol converted at the end of step (a) and the amount of glycerol used in step (a), is generally less than or equal to 5%, often less than or equal to 3%, more often less than 1% and frequently less than or equal to 0.1%.

The glycerol in the composition subjected to step (a) may have been produced starting from fossil raw materials and/or renewable raw materials, preferably starting from renewable raw materials, as described in WO 2005/054167 of SOLVAY SA, the content of which is incorporated herein by reference, and especially the passages from page 1, line 26, to page 4, line 2, and such as defined in Application WO 2006/100312 in the name of Solvay SA, from page 1, line 26 to page 2, line 5, the content of which is incorporated here by reference, and as described in WO2009/000773 of SOLVAY SA, the content of which is incorporated herein by reference, and especially the passages at page 10, lines 16 to 23, and at page 11, lines 4 to 25. Glycerol obtained starting from renewable raw materials is, for example, glycerol obtained in processes for conversion of animal or plant oils and/or fats, such as hydrolysis, saponification, transesterification, aminolysis or hydrogenation processes and enzymatic rupture processes, such as transesterification or hydrolysis with lipase-type enzymes, such as described in "Medium and Long-Term Opportunities and Risks of the Biotechnological Production of Bulk Chemicals from Renewable Resources, The Potential of White Biotechnology, The BREW Project, Final report Prepared under the European Commission's GROWTH Programme (DG Research), Utrecht, September 2006, pp. 29-31". Glycerol obtained starting from renewable raw materials is, for example, glycerol obtained in processes for conversion of mono- and polysaccharides and derived alcohols, such as fermentation, and thermochemical processes such as hydrogenation and hydrogenolysis, as described in "Industrial Bioproducts: Today and Tomorrow, Energetics, Incorporated for the U.S. Department of Energy, Office of Energy Efficiency and Renewable Energy, Office of the Biomass Program, July 2003, pages 49, 52 to 56". Mono- and polysaccharides, such as for example, starch, cellulose, hemicellulose, sucrose, lactose, glucose, galactose, maltose, allose, altrose, mannose, gulose, idose, talose, xylose, arabinose, ribose and lyxose may themselves be obtained from biomass.

In the process according to the invention, the treatment from optional step c) may be chosen from evaporative concentration, evaporative crystallization, distillation, fractional distillation, stripping and liquid/liquid extraction operations and combinations of at least two of these operations.

This treatment may be carried out under reduced pressure.

The term "evaporative concentration" is understood to mean a process of partial evaporation of the product which makes it possible to concentrate the residual product to less volatile entities. The term "evaporative crystallization" is understood to mean a process resulting in the crystallization of a compound by removing, by vaporization, a compound that promotes its dissolution in the medium. These processes are described in "Perry's Chemical Engineers' Handbook" in the $11^{th}$ section of the $7^{th}$ edition.

The term "distillation" is understood to mean the type of separation conventional in chemical engineering and described, for example, in "Perry's Chemical Engineers' Handbook" in the $13^{th}$ section of the $7^{th}$ edition.

The term "fractional distillation" is understood to mean a series of distillations where the distillate is withdrawn batchwise.

The term "stripping" is understood to mean the separation of a substance by entrainment using the vapour of a pure material. In the process according to the invention, this material can be any compound which is inert with respect to glycerol, such as, for example, steam, air, nitrogen and carbon dioxide.

The term "liquid/liquid extraction" is understood to mean bringing into contact with an appropriate completely or partially immiscible solvent that makes it possible to selectively extract the desired compounds, optionally according to a countercurrent process, as described in "Perry's Chemical Engineers' Handbook" in the 15$^{th}$ section of the 7$^{th}$ edition.

The stripping, evaporative concentration, evaporative crystallization, liquid/liquid extraction and distillation treatments may be combined, for example in a stripping column surmounted by a distillation section or in a partial evaporator supplying a distillation column or by combining a liquid/liquid extraction, stripping of the residual solvent contained in the glycerol-enriched stream and distillation of the solvent enriched with extracted compounds.

The diols, monoalcohols and the glycerol alkyl ethers are recovered in the first distilled, evaporated or stripped fraction, the purified glycerol-based composition comprising at least one cyclic oligomer of glycerol according to the invention constitutes an intermediate cut from the distillation, evaporation or stripping treatment. Glycerol containing non cyclic glycerol oligomers constitute the residue from the treatment of step (c) of the invention.

When the treatment consists of a partial evaporation of the product, the temperature of the intermediate cut from the glycerol-rich distillation treatment is generally greater than or equal to 0° C., often greater than or equal to 80° C. and frequently greater than or equal to 100° C. This temperature is generally less than or equal to 280° C., often less than or equal to 250° C., and frequently less than or equal to 200° C. The boiling point of the first glycerol-depleted distilled fraction is generally greater than or equal to −20° C., often greater than or equal to −10° C., frequently preferably greater than or equal to 0° C. This temperature is generally at most equal to the temperature of the intermediate cut from the glycerol-rich distillation treatment, often at least 5° C. below this temperature, particularly at least 10° C. below this temperature.

When the treatment is carried out by liquid/liquid extraction, the temperature is generally greater than or equal to 20° C., often greater than or equal to 40° C., and frequently greater than or equal to 50° C. This temperature is generally less than or equal to 200° C., often less than or equal to 150° C. and particularly less than or equal to 120° C.

The treatment pressure is generally greater than or equal to 0.001 mbar. This pressure is generally less than or equal to 1 bar, often less than or equal to 0.5 bar, frequently less than or equal to 0.3 bar and more specifically less than or equal to 0.25 bar. When the treatment comprises a separate evaporation step, the latter is generally carried out at a pressure less than or equal to 2 bar absolute, often at a pressure less than or equal to 1 bar absolute, and frequently at a pressure less than or equal to 0.5 bar absolute. It is generally carried out at a pressure greater than or equal to 0.1 mbar, often at a pressure greater than or equal to 0.2 mbar. When the evaporation step is combined with a distillation or fractional distillation step, it is carried out at a pressure at least equal to the pressure of the step carried out at the lowest pressure, often at a pressure at least 10 mbar greater than the pressure of the step carried out at the lowest pressure. The stripping step is generally carried out at a pressure less than or equal to 5 bar, frequently less than or equal to 2 bar.

In the distillation treatments with or without stripping, the reflux ratio is generally greater than or equal to 1%, often greater than or equal to 5% and frequently greater than or equal to 10%. This reflux ratio is less than or equal to 99% and often less than or equal to 50%. The expression "reflux ratio" is understood to mean, for a continuous distillation, the flow of the vaporized fraction to the reboiler over the flow of the residue.

The expression "reflux ratio" is understood to mean, for a batchwise, fractional distillation, the ratio of the amount vaporized relative to the final residue.

The amount of the fraction distilled is generally less than or equal to 300 g/kg, often less than or equal to 100 g/kg of the composition comprising glycerol.

The distillation, fractional distillation or stripping treatment may be preceded or followed by an operation which may, for example, be a settling, centrifugation, filtration, adsorption or ion-exchange operation. When it is a settling operation, the operation can be improved by passing through a coalescer. The adsorption operation is often an operation for adsorption on activated carbon.

The invention furthermore relates to a process for manufacturing dichloropropanol in which at least one composition comprising glycerol and at least one cyclic oligomer of glycerol at a content greater than or equal to 0.01 and less than or equal to 20 g of cyclic oligomer/kg of composition, is reacted with a chlorinating agent.

The invention also relates to the use of a composition comprising glycerol and at least one cyclic oligomer of glycerol at a content greater than or equal to 0.01 and less than or equal to 20 g of cyclic oligomer/kg of composition, for the manufacture of dichloropropanol.

The composition comprising glycerol and at least one cyclic oligomer of glycerol at a content greater than or equal to 0.01 and less than or equal to 20 g of cyclic oligomer/kg of composition may be as described above.

In the process for manufacturing dichloropropanol according to the invention, the chlorinating agent generally comprises hydrogen chloride. The hydrogen chloride can be gaseous hydrogen chloride, an aqueous hydrogen chloride solution or a mixture of the two. The chlorinating agent is preferably gaseous hydrogen chloride.

In the process for manufacturing dichloropropanol according to the invention, the chlorinating agent may be such as described in Patent Applications WO 2007/144335, from page 12, line 34 to page 13, line 35, WO 2005/054167, from page 4, line 32 to page 5, line 18, and WO 2006/106153, from page 2, line 10 to page 3, line 20, all in the name of SOLVAY SA, the contents of which are incorporated here by reference.

When the chlorinating agent is hydrogen chloride, the hydrogen chloride may be purified such as described in FR 08/56138 of SOLVAY SA, the content of which is incorporated herein by reference, especially the passages from page 2, line 33, to page 16, line 21.

In the process for manufacturing dichloropropanol according to the invention, the reaction with the chlorinating agent may be carried out in a reaction medium such described in WO 2006/106154 of SOLVAY SA, the content of which is incorporated herein by reference, especially the passages from page 14, line 15, to page 17, line 10.

In the process for manufacturing dichloropropanol according to the invention, the composition comprising the glycerol and the cyclic oligomer of glycerol may be treated such described in FR 08/58362 of SOLVAY SA, the content of which is incorporated herein by reference, especially the passages from page 6, line 4, to page 11, line 26.

In the process for manufacturing dichloropropanol according to the invention, the reaction with the chlorinating agent may be carried out in the presence of a catalyst, preferably a carboxylic acid or a carboxylic acid derivative, such as described in Patent Application WO 2005/054167, from page 6, line 24 to page 7, line 35 in the name of SOLVAY SA, and in Application WO 2006/020234, from page 8, line 24 to page 9, line 10, and from page 13, line 1 to page 18, line 3, the contents of which are incorporated here by reference. Succinic, glutaric, adipic, suberic, sebacic, dodecanoic, citric and butanetetracarboxylic acids and derivatives thereof such as acid chlorides, anhydrides, esters, salts, amides and nitriles are examples of catalysts.

In the process for manufacturing dichloropropanol according to the invention, the reaction with the chlorinating agent may be carried out for a catalyst concentration, at a temperature, at a pressure and at a residence time such described in WO 2005/054167 of SOLVAY SA, the content of which is incorporated herein by reference, especially the passages from page 8, line 1, to page 10, line 10.

In the process for manufacturing dichloropropanol according to the invention, the reaction with the chlorinating agent may be carried out such described in WO 2007/054505 of SOLVAY SA, the content of which is incorporated herein by reference, especially the passages from page 1, line 24 to page 6, line 18.

In the process for manufacturing dichloropropanol according to the invention, the reaction with the chlorinating agent may be carried out in the presence of a solvent such described in WO 2005/054167 of SOLVAY SA, the content of which is incorporated herein by reference, especially the passages at page 11, line 12 to 36. Oligomers of glycerol are not considered as such by-products.

In the process for manufacturing dichloropropanol according to the invention, the reaction with the chlorinating agent may be carried out in the presence of a liquid phase comprising heavy compounds other than glycerol such described in WO 2006/100316 of SOLVAY SA, the content of which is incorporated herein by reference, especially the passages at page 2, lines 18 to 25 and from page 15, line 32, to page 17, line 33.

In the process for manufacturing dichloropropanol according to the invention, the reaction with the chlorinating agent may be carried out under stirring with a stirring system such described in WO2008/145729 of SOLVAY SA, the content of which is incorporated herein by reference, especially the passages from page 1, line 30, to page 2, line 33, and from page 6, line 22, to page 14, line 31.

In the process for manufacturing dichloropropanol according to the invention, the reaction with the chlorinating agent may be carried out in a liquid reaction medium such described in WO 2006/106154 of SOLVAY SA, the content of which is incorporated herein by reference, especially the passages from page 1, line 29, to page 2, line 6, and from page 14, line 15, to page 17, line 10.

In the process for manufacturing dichloropropanol according to the invention, the reaction with the chlorinating agent may be carried out in a reactor the feeding of which is described in WO 2008/107468 of SOLVAY SA, the content of which is incorporated herein by reference, especially the passages from page 1, line 29, to page 4, line 27, and from page 5, line 34, to page 9, line 17.

The process for manufacturing dichloropropanol according to the invention may be carried in equipments made of or coated with materials which are resistant to the corrosion by the chlorinating agent under the process conditions, such as described in WO 2005/054167 of SOLVAY SA, the content of which is incorporated herein by reference, especially the passages from page 6, line 3 to 23.

The process for manufacturing dichloropropanol according to the invention may be carried in equipments made of or coated with materials which are resistant to the corrosion by the chlorinating agent under the process conditions, such as described in WO 2006/100317 of SOLVAY SA, the content of which is incorporated herein by reference, especially the passages from page 23, line 22, to page 27, line 25.

Polyaryletheretherketones (PEEK) and copolymers of ethylene and chlorotrifluoroethylene (E-CTFE) are examples of polymers which are particularly convenient as material for equipments for the process for manufacturing dichloropropanol by hydrochlorination of glycerol.

The process for manufacturing dichloropropanol according to the invention may be carried in equipments made of or coated with materials which are resistant to the corrosion by the chlorinating agent under the process conditions, such as described in PCT/EP2008/062845 of SOLVAY SA, the content of which is incorporated herein by reference, especially the passages from page 1, line 30, to page 9, line 17, and from page 19, line 25, to page 20, line 33.

In the process for manufacturing dichloropropanol according to the invention, the chlorination reaction is preferably carried out in a liquid reaction medium.

In the process for manufacturing dichloropropanol according to the invention, the chlorination reaction may be carried out in the presence of a solvent.

In the process for manufacturing dichloropropanol according to the invention, the dichloropropanol formed can be separated from the other constituents of the reaction medium by any separation treatment, for example by distillation, stripping, extraction or adsorption. After this treatment, the other constituents of the reaction medium may be subjected to supplementary separation treatments. Among the other constituents of the reaction medium are heavy products such as, for example, various chlorinated and/or esterified isomers of glycerol oligomers. The chlorinated and/or esterified isomers of glycerol oligomers and, in particular, the chlorinated and/or esterified cyclic glycerol oligomers and more particularly the chlorinated and/or esterified cyclic dimers of glycerol furthermore contribute significantly to the increase in the content of heavy compounds of the reaction medium, necessitating an increase in the frequency of the purges of the reaction medium.

The advantage of using a composition comprising glycerol and cuclic oligomers of glycerol according to the invention for the manufacture of dichloropropanol is the controlled formation of these heavy products, in particular of chlorinated and/or esterified oligomers of glycerol, more particularly of chlorinated and/or esterified cyclic oligomers of glycerol, and still more particularly of chlorinated and/or esterified cyclic dimers of glycerol with, as a result, a reduction in the frequency of the purging operations.

In the process for manufacturing dichloropropanol according to the invention, a separation of dichloropropanol from the other compounds of the reaction mixture may be carried out such described in WO 2005/054167 of SOLVAY SA, the content of which is incorporated herein by reference, especially the passages from page 12, line 1, to page 17, line 20.

In the process for manufacturing dichloropropanol according to the invention, a separation of dichloropropanol from the other compounds of the reaction mixture may be carried out such described in WO 2006/100312 of SOLVAY SA, the content of which is incorporated herein by reference, especially the passages at page 2, lines 3 to 10, at page 20, line 28 to page 28, line 20.

In the process for manufacturing dichloropropanol according to the invention, a separation of dichloropropanol from the other compounds of the reaction mixture may be carried out according to methods such described in WO 2006/100313 of SOLVAY SA, the content of which is incorporated herein by reference, especially the passages at page 2, lines 1 to 23, and from page 21, line 7, to page 25, line 25.

In the process for manufacturing dichloropropanol according to the invention, a separation of dichloropropanol from the other compounds of the reaction mixture may be carried out according to methods such described in WO 2006/100314 of SOLVAY SA, the content of which is incorporated herein by reference, especially the passages at page 2, lines 6 to page 3, line 4, and from page 18, line 33, to page 22, line 29.

In the process for manufacturing dichloropropanol according to the invention, a separation of dichloropropanol from the other compounds of the reaction mixture may be carried out according to methods such described in WO 2006/100320 of SOLVAY SA, the content of which is incorporated herein by reference, especially the passages from page 1, line 30, to page 2, line 23 and from page 6, line 25, to page 10, line 28.

In the process for manufacturing dichloropropanol according to the invention, a separation of dichloropropanol from the other compounds of the reaction mixture may be carried out according to methods such described in WO 2006/100315 of SOLVAY SA, the content of which is incorporated herein by reference, especially the passages at page 2, lines 3 to 29, and from page 23, line 3, to page 24, line 13.

In the process for manufacturing dichloropropanol according to the invention, a separation of dichloropropanol from the other compounds of the reaction mixture may be carried out according to methods such described in WO2008/110588 of SOLVAY SA, the content of which is incorporated herein by reference, especially the passages from page 1, line 31, to page 27, line 25.

In the process for manufacturing dichloropropanol according to the invention, the dichloropropanol is generally obtained as a mixture of 1,3-dichloropropan-2-ol and 2,3-dichloropropan-1-ol isomers such described in WO 2006/100319 of SOLVAY SA, the content of which is incorporated herein by reference, especially the passages from page 23, line 34, to page 24, line 29.

In the process for manufacturing dichloropropanol according to the invention, the dichloropropanol may contain halogenated ketones such described in WO 2006/100311 of SOLVAY SA, the content of which is incorporated herein by reference, especially the passages at page 2, lines 22 to 34, and from page 22, line 8, to page 23, line 35.

In the process for manufacturing dichloropropanol according to the invention, water which have been in contact with equipment walls may be treated such described in FR 08/56059 of SOLVAY SA, the content of which is incorporated herein by reference, especially the passages from page 1, line 7, to page 16, line 34.

In addition, the invention relates to a process for manufacturing epichlorohydrin in which the dichloropropanol obtained according to the process for manufacturing dichloropropanol according to the invention, is subjected to a dehydrochlorination reaction.

The process for manufacturing epichlorohydrin by dehydrochlorination of dichloropropanol according to the invention may be carried out under conditions such as described in the International application WO 2005/054167 in the name of SOLVAY SA, the content of which is incorporated herein by reference, more specifically, the passage on page 19, line 12 to page 22, line 30.

The process for manufacturing epichlorohydrin by dehydrochlorination of dichloropropanol according to the invention may be carried out under conditions such as described in the International application WO 2006/100311 in the name of SOLVAY SA, the content of which is incorporated herein by reference, more specifically, the passage on page 2, lines 22 to 25, and on page 22, line 28 to page 23, line 35.

The process for manufacturing epichlorohydrin by dehydrochlorination of dichloropropanol according to the invention may be carried out under conditions such as described in the International application WO 2008/101866 in the name of SOLVAY SA, the content of which is incorporated herein by reference, more specifically, the passage from page 2, line 1 to page 13, line 16.

The process for manufacturing epichlorohydrin by dehydrochlorination of dichloropropanol according to the invention may be carried out under conditions such as described in the International application WO 2008/152045 in the name of SOLVAY SA, the content of which is incorporated herein by reference, more specifically, the passage from page 9, line 22 to page 13, line 31.

The process for manufacturing epichlorohydrin by dehydrochlorination of dichloropropanol according to the invention may be carried out under conditions such as described in the International application WO 2008/152043 in the name of SOLVAY SA, the content of which is incorporated herein by reference, more specifically, the passage from page 6, line 16 to page 7, line 22.

The process for manufacturing epichlorhydrin by dehydrochlorination of dichloropropanol according to the invention may be integrated in a global scheme for preparing a chlorohydrin such as described in WO 2006/106155 in the name of SOLVAY SA, the content of which is hereby incorporated by reference, more specifically the passages at page 2, lines 26 to 31, and from page 22, line 10 to page 23, line 19.

The process for manufacturing epichlorhydrin by dehydrochlorination of dichloropropanol according to the invention may also be carried out such as described in WO 2006/100318 in the name of SOLVAY SA, the content of which is hereby incorporated by reference, more specifically the passages at page 2, lines 23 to page 3, line 26, and from page 24, line 17 to page 31, line 18.

The process for manufacturing epichlorhydrin by dehydrochlorination of dichloropropanol according to the invention may also comprise a step of treating water effluents such as described in EP 08150925.9 in the name of SOLVAY SA, the content of which is hereby incorporated by reference, more specifically the passages from page 1, line 18 to page 12, line 10.

In the process for manufacturing epichlorhydrin by dehydrochlorination of dichloropropanol according to the invention, another part of the dichloropropanol may be obtained by a process other than glycerol chlorination. This process may be chosen from allyl chloride hypochlorination and allyl alcohol chlorination processes.

Moreover, the invention relates to epichlorohydrin which may be obtained by subjecting the dichloropropanol obtained according to the invention to a dehydrochlorination reaction.

The epichlorohydrin according to the invention comprises generally at least one other compound, as an impurity, that epichlorohydrin itself. That compounds can be selected from:
compounds of crude formula $C_3H_3Cl_3$, $C_4H_7ClO$, $C_4H_7ClO_2$, $C_4H_8O$, $C_5H_{10}O$, $C_6H_8O_2$, $C_6H_9Cl_3$, $C_6H_9Cl_3O_2$, $C_6H_{10}O$, $C_6H_{10}O_3$, $C_6H_{10}Cl_2$, $C_6H_{12}O$, $C_6H_{13}Br$, $C_6H14O$, $C_7H_{10}O$, $C_7H_{14}O_2$, $C_9H_9Cl_3$, $C_9H_{10}O_2$, $C_9H15Cl_5O$, $C_9H_{15}Cl_2O_2$ and $C_9H_{17}Cl_3O_4$
hydrocarbons, in particular, methylcyclopentane and ethylbenzene
ketones, in particular, acetone, cyclopentanone, 2-butanone, cyclohexanone, 2,3-pentanedione, 2-methyl-2-cyclopenten-1-one, 3,5-dimethyl-2-cyclohexene-1-one, ketones of crude formula $C_5H_{10}O$, $C_6H_{12}O$ and $C_9H_{10}O_2$, 1-phenoxy-2-propanone, hydroxyacetone halogenated ketones comprising from 3 to 18 carbon atoms, more specifically, chlorinated ketones and yet more specifically, chloroacetone and chlorobutanones, aldehydes, in particular, acetaldehyde, isobutanal, isopentanal, hexanal and acrolein, ethers, in particular
- chloroethers, more specifically chlorinated ethers of crude formula $C_6H_{13}ClO_4$, $C_6H_{10}Cl_2O_2$, $C_6H_{12}Cl_2O$, $C_6H_{12}Cl_2O_3$, $C_6H_{12}Cl_2O_3$ and $C_6H_{11}Cl_3O_2$,
- alkyl glycidyl ethers, more specifically, methyl glycidyl ether, ethyl glycidyl ether, propyl glycidyl ethers, butyl glycidyl ethers, diglycidyl ether, and yet more specifically methyl glycidyl ether,
- cyclic ethers and more specifically oxetane and epoxides among which more specifically glycidol, bromoepoxypropane, dichloroepoxypropane, 1,2-epoxyhexane, propylene oxide and 2,3-epoxy-butane, alcohols, more specifically
- aliphatic alcohols, such as 1-propanol, 2-propanol, allyl alcohol and glycerol,
- aromatic alcohols such as phenol, halogenated hydrocarbons, more specifically halogenated aliphatic hydrocarbons, and still more specifically,
- bromochloromethanes, such as dibromochloromethane,
- chloromethanes such as dichloromethane, trichloromethane and tetrachloromethane,
- dichloroethanes such as 1,1-dichloroethane and 1,2-dichloroethane,
- trichloropropanes, such as 1,2,3-trichloropropane, 1,1,3-trichloropropane, 1,1,2-trichloropropane ans 1,2,2-trichloropropane,
- dichloropropanes such as 1,3-dichloropropane, 1,2-dichloropropane and 2,2-dichloropropane,
- monochloropropanes such as 2-chloropropane and 1-chloropropane,
- trichloropropenes such as 1,3,3-trichloropropenes cis and trans, 1,2,3-trichloropropenes cis and trans, and 1,1,3-trichloropropene,
- dichloropropenes such as 1,3-dichloro-1-propenes cis and trans, 3,3-dichloro-1-propene and 2,3-dichloro-1-propene,
- monochloropropenes, such as 2-chloro-1-propene, 1-chloro-1-propene cis and trans and 3-chloro-1-propene, halogenated hydrocarbons, more specifically halogenated aromatic hydrocarbons, and yet more specifically
- chlorobenzenes, such as monochlorobenzene, dichlorobenzenes, trichlorobenzenes, tetrachlorobenzenes, pentachlorobenzene and hexachlorobenzene,
- chloronaphthalenes, such as monochloronaphthalenes, dichloronaphthalenes, trichloronaphthalenes, tetrachloronaphthalenes, pentachloronaphthalenes and hexachloronaphthalenes, chloroalcools, more specifically,
- 2-chloroethanol,
- monochloropropanediols, such as 3-chloro-1,2-propanediol and 2-chloro-1,3-propanediol,
- dichloropropanols, such as 1,3-dichloro-2-propanol and 2,3-dichloro-1-propanol
- bromochloropropanols
- monochloropropanols, such as 3-chloro-1-propanol,
- monochloropropenols such as 2-chloro-2-propene-1-ol and 3-chloro-2-propene-1-ol cis and trans water, salts such as sodium chloride, calcium chloride and sodium hydroxide.

The contents of those impurities in the epichlorohydrin according to the invention are such as described in the International application WO 2006/100311 of SOLVAY SA, the content of which is incorporated herein by reference, more specifically the passage from page 22, lines 8 to 12.

The contents of those impurities in the epichlorohydrin according to the invention are such as described in the International application WO 2008/101866 of SOLVAY SA, the content of which is incorporated herein by reference, more specifically passages from page 13, line 28, to page 16, line 15, on page 16, lines 28 to 33, and on page 17, lines 10 to 13, and in Table 1, page 21, in Table 2, page 22, in Table 3, page 23, in Table 4, page 24, and in Table 6, page 25 and 26.

The contents of those impurities in the epichlorohydrin according to the invention are such as described in the International application WO 2008/152045 of SOLVAY SA, the content of which is incorporated herein by reference, more specifically passages from page 2, line 29, to page 9, line 21, from page 14, line 1 to page 17, line 14, and in Table 1, pages 63 and 64, in Table 6, pages 70 and 71, and in Table 7, pages 74 and 75.

The contents of those impurities in the epichlorohydrin according to the invention are such as described in the International application WO 2008/152044 of SOLVAY SA, the content of which is incorporated herein by reference, more specifically passages on page 2, line 14 to page 10, line 14, and in Table 1, pages 44 and 45, in Table 6, pages 51 and 52, and in Table 7, pages 55 and 56.

The content of compound of crude formula $C_4H_7ClO$ in the epichlorohydrin according to the invention is generally higher than or equal to 0.001 mg/kg. This content is generally lower than or equal to 0.5 g/kg, often lower than or equal to 0.1 g/kg, frequently lower than or equal to 0.05 g/kg and more specifically lower than or equal to 0.01 g/kg.

The content of compound of crude formula $C_5H_{10}O$ in the epichlorohydrin according to the invention is generally higher than or equal to 0.001 mg/kg. This content is generally lower than or equal to 0.5 g/kg, often lower than or equal to 0.1 g/kg, frequently lower than or equal to 0.05 g/kg and more specifically lower than or equal to 0.01 g/kg.

The content of compound of crude formula $C_6H_{10}O_3$ in the epichlorohydrin according to the invention is generally higher than or equal to 0.001 mg/kg. This content is generally lower than or equal to 0.5 g/kg, often lower than or equal to 0.1 g/kg, frequently lower than or equal to 0.05 g/kg and more specifically lower than or equal to 0.01 g/kg.

The content of compound of crude formula $C_6H_{12}O$ in the epichlorohydrin according to the invention is generally higher than or equal to 0.001 mg/kg. This content is generally lower than or equal to 0.5 g/kg, often lower than or equal to 0.1 g/kg, frequently lower than or equal to 0.05 g/kg and more specifically lower than or equal to 0.01 g/kg.

The content of 2,3-pentanedione in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of chlorobutanone in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of hexanal in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of chloroether of crude formula $C_6H_{13}ClO_4$ in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of chloroether of crude formula $C_6H_{12}Cl_2O_3$ in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of diglycidyl ether in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of 1-propanol in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of 1,1-dichloroethane in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of bromochloropropanols in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The content of bromoepoxypropane in the epichlorohydrin according to the invention is generally higher than or equal to 0.001 mg/kg. This content is generally lower than or equal to 0.8 g/kg, usually lower than or equal to 0.6 g/kg, in many cases lower than or equal to 0.5 g/kg, often lower than or equal to 0.4 g/kg, commonly lower than or equal to 0.2 g/kg, frequently lower than or equal to 0.05 g/kg, specifically lower than or equal to 0.01 g/kg, and more specifically lower than or equal to 0.001 g/kg.

The invention also relates to a process for manufacturing epoxy resins or glycidyl ethers or glycidyl esters or glycidyl amides or glycidyl imides or glycidyl amines or products that can be used as coagulants or water-resistant resins or cationization agents or flame retardants or ingredients for detergents or epichlorohydrin elastomers or halogenated polyethers-polyols or monochloropropanediol, preferably 3-chloro-1,2-propanediol, in which the epichlorohydrin according to the invention is subjected to a reaction with at least one compound chosen from monoalcohols, monocarboxylic acids, polyols, polyamines, amino alcohols, polyimides, polyamides, polycarboxylic acids, ammonia, amines, polyaminoamides, polyimines, amine salts, phosphoric acid, phosphoric acid salts, phosphorus oxychlorides, phosphoric acid esters, phosphonic acids, esters of phosphonic acids, salts of phosphonic acids, phosphinic acids, esters of phosphinic acids, salts of phosphinic acids, phosphine oxides, phosphines, ethoxylated alcohols, alkylene or phenylene oxides, and mixtures of at least two of these compounds, or in which the epichlorohydrin according to the invention is subjected to a homopolymerization reaction or in which epichlorohydrin is subjected to a reaction of oligomerisation, of co-oligomerisation, of condensation, of dehydrochlorination and of hydrolysis, with water, or with a di- or polyhydroxylated compound which may optionally be halogenated and/or have ether oxide bonds and/or double bonds capable of being halogenated in a subsequent stage or wherein epichlorohydrin according to the invention is subjected to a reaction with water.

In addition, the invention also relates to the use of the epichlorohydrin according to the invention in the manufacture of epoxy resins or glycidyl ethers or glycidyl esters or glycidyl amides or of glycidyl imides or of glycidyl amines or of products that can be used as coagulants or water-resistant resins or cationization agents or flame retardants or ingredients for detergents or epichlorohydrin elastomers or of halogenated polyethers-polyols or monochloropropanediol, preferably 3-chloro-1,2-propanediol.

Epoxy resins or glycidyl ethers or glycidyl esters or glycidyl amides or of glycidyl imides or of glycidyl amines or of products that can be used as coagulants or water-resistant resins or cationization agents or flame retardants or ingredients for detergents or epichlorohydrin elastomers, may be obtained according to processes such as described in International application WO 2008/152045 in the name of SOLVAY SA, the content of which is incorporated herein by reference, more specifically the passage from page 32, line 6 to page 62, line 34.

Epoxy resins or glycidyl ethers or glycidyl esters or glycidyl amides or of glycidyl imides or of glycidyl amines or of products that can be used as coagulants or water-resistant resins or cationization agents or flame retardants or ingredients for detergents or epichlorohydrin elastomers, may be obtained according to processes such as described in International application WO 2008/152044 in the name of SOLVAY SA, the content of which is incorporated herein by reference, more specifically the passage from page 13, line 22, to page 44, line 8.

The halogenated polyethers-polyols can be used in the manufacture of rigid or semi-rigid polyurethane foams, more specifically in the manufacture of such fireproof polyurethane foams.

The halogenated polyethers-polyols can be obtained by processes such as described in French patent application 2180138 in the name of SOLVAY & Cie, the content of which is incorporated herein by reference, more specifically the passage from page 4, line 24, to page 7, line 19.

The chlorinated polyether polyols forming the object of the invention may be obtained by oligomerisation, co-oligomerisation, condensation, dehydrochlorination, and hydrolysis, the starting materials comprising on the one hand epichlorohydrin and on the other hand water or di- or polyhydroxylated compounds which may optionally be halogenated and/or have ether oxide bonds, and/or double bonds capable of being halogenated in a subsequent stage according to techniques well known to those versed in the art.

A suitable mode of operation comprises hydrolysis in a diluted acid medium of di- or polyglycidyl ethers of epichlorohydrin oligomers of the general formula:

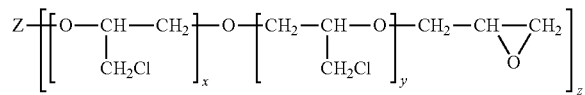

in which z is a number between 2 and 6, x and y represent numbers between 0 and 12 such that the mean value x+y per chain is between 0 and 12 and that z (x+y), in which x+y represents the mean value of x+y in the entire molecule, is between 1 and 72, and Z represents an optionally halogenated saturated or unsaturated organic radical of valence z.

This hydrolysis may be accompanied by secondary condensation reactions which lead to a lengthening of the chains with the formation of chlorinated polyether polyols containing more chlorine and less hydroxyl functions.

It is not indispensable to separate these products, which are likewise chlorinated polyether polyols containing alpha-diol groups, the presence of which is not in any way harmful to the synthesis of further processed products.

The hydrolysis of di- and polyglycidyl ethers of epichlorohydrin oligomers is advantageously effected in a nitric or perchloric acid medium.

The amounts of water and acid to be used for the hydrolysis may vary to a considerable extent. They govern in particular the reaction period and also the rate of the secondary condensation reactions. It is advantageous to use from $1.2 \times 10^{-2}$ to $2.5 \times 10^{-2}$ moles of nitric acid and from 1 to 10 kg of water per mole of di- or polyglycidyl ether.

The hydrolysis reaction is carried out with agitation at the boiling temperature of the reaction medium. The end of the reaction is detected by determination of the residual oxirannic oxygen.

After cooling, the reaction product may be in the form of a two-phase system, comprising an aqueous phase containing the chlorinated polyether polyols which are the lightest and have the most hydroxyl functions, and a dense water-saturated organic phase containing the halogenated polyether polyols which are the heaviest and contain the most halogen. It is not indispensable to separate these two phases and to treat them separately in order to isolate the polyether polyols which they contain.

The mode of operation described above is suitable for the production of polyether polyols halogenated "to measure" which have variable relative contents of halogen and hydroxyl functions which are determined by appropriate choice of the initial glycidyl ether and/or of the hydrolysis conditions.

The di- and polyglycidyl ethers of epichlorohydrin oligomers are obtained, in a manner known per se, by dehydrochlorination in a alkaline medium of chlorinated polyether polyols having end chlorohydrin groups resulting from the oligomerisation of epichlorohydrin which is initiated by water or a di- or polyhydroxyl compound, which may be saturated or unsaturated, halogenated or non-halogenated, and of an aliphatic, alicyclic, or aromatic nature.

A first type of di- and polyglycidyl ethers according to the formula above comprises those the formula of which contains a non-halogenated radical Z. They are obtained by dehydrochlorination of chlorinated polyether polyols resulting from the catalytic oligomerisation of epichlorohydrin which is initiated by saturated or unsaturated polyols, such as ethyleneglycol, propyleneglycol, and hexamethyleneglycol, glycerine, butanetriol and hexanetriol, trimethylolpropane, erythritol and pentaerythritol, mannitol and sorbitol, resorcinol, catechol, hydroquinone, bisphenol A, di- and tri-ethyleneglycol, di- or tri-propyleneglycol, 2-butene-1,4-diol, 3-butene-1,2-diol, 2 butyene-1,4-diol, 3-butyne-1,2-diol, 1,5-hexadiene-3,4-diol, 2,4-hexadiene-1,6-diol, 1,5-hexadiyne-3,4-diol, 2,4-hexadiyne-1,6-diol.

The polyols which are particularly preferred are the aliphatic polyols, particularly 2-butene-1,4-diol and 2-butyne-1,4-diol, ethylene glycol, and glycerine. The use of these last-mentioned initiators leads to the obtaining of di- and polyglycidyl ethers corresponding to the general formula given above in which Z represents the radicals respectively.

A second type of di- and polyglycidyl ethers leading to polyether polyols having a higher halogen content comprises those of which the formula given above contains a halogenated radical Z, the halogen being selected from the group comprising chlorine and bromine. They may be obtained by the dehydrochlorination of the chlorinated polyether polyols resulting from the catalytic oligomerisation of epichlorohydrine which is initiated by saturated or unsaturated halogenated polyols, such as glycerol monochloro- and monobromohydrins, 3,4-dibromo-1,2-butanediol, 2,3-dibromo-1,4-butanediol, the 2,3-dibromo-2-butene-1,4-diols, the 3,4-dibromo-2-butene-1,2-diols, 2,2(bis) bromomethyl-1,3-propanediol, 1,2,5,6-tetrabromo-3,4-hexanediol.

The oligomerisation of epichlorohydrin may also be initiated by a mixture of brominated and/or unsaturated diols.

The molar ratio of epichlorohydrin and initiator polyol is not critical and may vary within a wide range. This ratio governs the hydroxyl index of the resulting polyether polyol.

The oligomerisation catalyst may be any of the acid catalysts known for this type of reaction. It is nevertheless preferred to use boron trifluoride in the free or complexed state.

Di- and polyglycidyl ethers of brominated epichlorohydrin oligomers can also be obtained by partial or complete molecular bromination of the di- or polyglycidyl ethers of unsaturated epichlorohydrin oligomers obtained by dehydrochloroination in an alkaline medium of the unsaturated chlorinated polyether polyols resulting from the catalytic oligomerisation of epichlorohydrin which is initiated by an unsaturated di- or polyhydroxyl compound.

Furthermore, the halogen content of the polyether polyols of the invention, and consequently the flame resistance of the polyurethanes derived therefrom, can be still further increased if these polyether polyols also have unsaturations, by partial or complete bromination of these unsaturations. By this technique the unsaturated polyols resulting from the hydrolysis is a dilute acid medium of the di- or polyglycidyl ethers of unsaturated epichlorohydrin oligomers of the general formula:

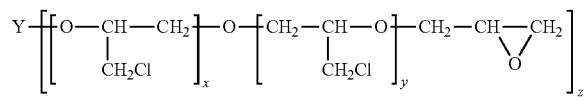

in which x, y, and z correspond to the definition given above and Y represents an unsaturated organic radical or valence z, are brominated.

The method of bromination of the polyether polyols and glycidyl ethers is not critical. It is possible to operate in a manner known per se, optionally in the presence of a catalyst and of an inert solvent such as chloroform, carbon tetrachloride, methylene chloride, or o-dichlorobenzene.

The temperature is generally kept below 50-60° C.

The amount of bromine used is not critical. Nevertheless, it is preferred to use an almost stoichiometric quantity of bromine.

Particularly preferred polyether polyols correspond to the general formula in which Z represents the radicals $CH_2Cl$—$CH(CH_2$—$)$—, —$CH_2$—$CHBr$—$CHBr$—$CH_2$—, —$CH_2$—$CBr$=$CBr$—$CH_2$—.

Monochloropropanediol, in particular 3-chloro-1,2-propanediol or α-monochlorohydrin of glycerol can be obtained according to a process such as described in U.S. Pat. No. 2,321,037, the content of which is incorporated herein by reference, more specifically the passage from page 2, left column, line 65 to page 3, left column, line 2.

The hydrolysis or hydration reaction of epichlorohydrin is carried out with water in the presence of an acid catalyst or an acid-acting catalyst, at a moderately high temperature.

The catalyst can be an acid, an acid salt, an acid-reacting substance or a substance capable of acting as an acid catalyst under the conditions of reaction. Suitable catalysts include strong mineral acids, such as sulfuric acid, phosphoric acid, metaphosphoric acid, phosphorous acid, pyrophosphoric acid, pyrosulfuric acid, nitric acid, perchloric acid. Other suitable compounds are for example, sulfuric oxychloride, sulfurous oxychloride, sulfurous oxybromide (thionyl bromide), nitrogen dioxide, nitrogen trioxide, nitrosyl chloride, phosphorous oxychloride, phosphorous trichloride, phosphorous pentachloride. Suitable inorganic acid-acting salts are for example, zinc sulfate, zinc phosphate, ferric sulfate, aluminum sulfate, sodium hydrogenosulfate, sodium mono- and dihydrogenophosphate. It is also possible to employ monobasic organic acids such as, formic, acetic, propionic, butyric, isobutyric, valeric, benzoic acids and their homologues and analogues. It is also possible to employ polybasic acids such as for example, oxalic, malonic, succinic acids, or hydroxyl and/or carbonyl substituted acids, such as lactic, citric, malic, mesoxalic acids. Furthermore, it is also possible to use organic esters, salts and compounds capable of acting as acid catalysts under the conditions of operation, such as for example, benzene sulfonic acid, and its homologues and analogues, dialkyl and alkyl acid sulfates, alkylated phosphoric and sulfonic acids, halogenated organic acids, acids such as sulfoacetic acid, acid halides and compounds like aniline-hydrochloride and the like. As a general rule, the use of a weaker acid catalyst ordinarily requires its application in higher concentrations or operation under higher temperatures in order to obtain the same degree of catalytic activity.

The hydrolysis or hydration of epichlorohydrin reaction temperature is generally comprised between 25 and 100° C. However, higher temperatures and shorter times of contact of the reactants may be resorted to when it is desirable to accelerate the reaction.

The hydration reaction can be carried out at any pressure, for example, at atmospheric pressure at the reflux temperature of the reaction mixture, or at a superatmospheric pressure when the temperature of the reaction mixture is around or higher than 100° C.

The hydrolysis of epichlorohydrin is generally carried out while maintaining a very high water to epoxide mol ration, this ratio being of at least of 10:1 and even higher.

The hydration of epichlorohydrin cane be carried out under continuous mode or under discontinuous mode.

The reaction mixture may be stirred or not.

The obtained reaction mixture comprising the reaction product, water and the acid catalyst cane be separated by any means, as for instance by a neutralization operation of the acid catalyst followed by a distillation operation.

In order to control the hydration reaction, it is preferable to introduce the epichlorohydrin gradually into the acid-containing water, thereby allowing an even and controllable hydration of the epichlorohydrin. The hydration reaction is effected by establishing a relatively large body of water containing the acid-acting catalyst, maintaining this aqueous solution at the described optimum temperature, and gradually introducing with stirring, the epichlorohydrin, the quantity of epichlorohydrin thus added being regulated so that the mol ratio of the water to the total epichlorohydrin introduced into the reaction vessel is at least, and preferably exceeds 10:1. After addition of the totality of the epichlorohydrin, the mixture is continuously agitated and maintained at the aforementioned moderate temperature for a period of time sufficient to allow the hydration reaction to occur, after which the desired products are separately recovered if it is preferred to obtain them in an anhydrous state.

The obtained reaction mixture may be first neutralized by the addition of an amount of a basic or basic-acting material, such as calcium carbonate, in a slight excess to the acid catalyst employed. As neutralizing basic agents it is preferable to employ basic or basic-acting materials which are themselves insoluble or substantially insoluble in the reaction mixture and which form insoluble or substantially insoluble salts.

The neutralized reaction mixture may then be distilled, preferably under a reduced pressure, under continuous or discontinuous mode. Under discontinuous mode, the first distillate is an aqueous phase which may comprise a small amount of monochloropropanediol, usually from 2 to 5% by weight and traces of epichlorohydrin and of dichloropropanol. This aqueous phase can be reused in further reactions of hydration of epichlorohydrin. The second distillate is made of 3-chloro-1,2-propanediol essentially anhydrous.

3-chloro-1,2-propanediol or α-monochlorohydrin of glycerol is an synthesis intermediate used for example in cosmetics and pharmaceutics for the manufacture of glycerol α-monoethers such as guafenesin (ether of glycerol and guaiacol), an expectorant added to cough syrups, and in the manufacture of α-monoesters (monoglycerides). This glycerol monochlorohydrin may also be used for the production of aminopropanediol derivatives, such as 3-amino-1,2-propanediol(isoserinol), starting material for the synthesis of X-ray contrasting agents. This glycerol monochlorohydrin may also be converted into glycidol used as a stabilizer in vinyl polymers and as intermediate for the manufacture of other chemicals. Finally, some quaternary ammonium compounds and polyhydroxy esters may also be obtained from this glycerol monochlorohydrin.

This invention furthermore relates to a process for manufacturing dichloropropanol in which glycerol is reacted with a chlorinating agent in a reaction medium wherein the ratio between the quantities of cyclic oligomers of glycerol and of the sum of the quantities of glycerol and of cyclic oligomers of glycerol, is greater than or equal to 0.01 and less than or equal to 20 g/kg.

The conditions for the process of manufacturing dichloropropanol are as described above.

The invention also relates to a process for manufacturing epichlorohydrin in which the dichloropropanol obtained in the previous mentioned process, is subjected to a dehydrochlorination reaction.

The conditions for the process of manufacturing epichlorohydrin are as described above.

The invention further relates to an epichlorhydrin which may be obtained from the previous process for manufacturing epichlorohydrin.

All the characteristics of that epichlorhydrin are as described above.

The invention also relates to a process for manufacturing epoxy resins or glycidyl ethers or glycidyl esters or glycidyl amides or glycidyl imides or glycidyl amines or products that can be used as coagulants or water-resistant resins or cationization agents or flame retardants or ingredients for detergents or epichlorohydrin elastomers or halogenated polyethers-polyols or monochloropropanediol, preferably 3-chloro-1,2-propanediol, comprising the previous process for manufacturing epichlorhydrin, in which the epichlorohydrin is subjected to a reaction with at least one compound chosen from monoalcohols, monocarboxylic acids, polyols, polyamines, amino alcohols, polyimides, polyamides, polycarboxylic acids, ammonia, amines, polyamino amides, polyimines, amine salts, phosphoric acid, phosphoric acid salts, phosphorus oxychlorides, phosphoric acid esters, phosphonic acids, esters of phosphonic acids, salts of phosphonic acids, phosphinic acids, esters of phosphinic acids, salts of phosphinic acids, phosphine oxides, phosphines, ethoxylated alcohols, alkylene or phenylene oxides, and mixtures of at least two of these compounds, or in which the epichlorohydrin is subjected to a homopolymerization reaction or in which the epichlorohydrin is subjected to a reaction of oligomerisation, of co-oligomerisation, of condensation, of dehydrochlorination and of hydrolysis, with water, or with a di- or polyhydroxylated compound which may optionally be halogenated and/or have ether oxide bonds and/or double bonds capable of being halogenated in a subsequent stage or wherein epichlorohydrin is subjected to a reaction with water.

The conditions for the process of manufacturing the epichlorohydrin derivatives are as described above.

The invention finally relates to the use of the epichlorohydrin obtainable in the previous process in the manufacture of epoxy resins or glycidyl ethers or glycidyl esters or glycidyl amides or glycidyl imides or glycidyl amines or of products that can be used as coagulants or water-resistant resins or cationization agents or flame retardants or ingredients for detergents or epichlorohydrin elastomers or halogenated polyethers-polyols or monochloropropanediol, preferably 3-chloro-1,2-propanediol. The examples below are intended to illustrate the invention without, however, limiting it.

EXAMPLE 1

According to the Invention

A mixture of glycerol and adipic acid containing 7.3% w/w adipic acid has been prepared by addition of adipic acid to glycerin containing 0.40 g/kg of diglycerol and 0.02 g/kg of cyclic diglycerol. Aqueous hydrochloric acid with a concentration of 5.8 mol of hydrogen chloride/kg of solution and the mixture of glycerol have been introduced at a constant flow rate of respectively 89.0 g/h and 25.8 g/h into a 350 ml glass reactor thermostatted at a temperature of 120° C. The reactor, which functioned at atmospheric pressure, was equipped with an overflow system for maintaining a constant volume of liquid. The reaction mixture fraction that was vaporized was evacuated from the reactor and condensed at ambient temperature. The condensate is a homogeneous aqueous phase containing most of the hydrochloric acid which had not reacted and a part of the dichloropropanol production. The liquid mixture collected at the overflow outlet contained the remainder of the dichloropropanol production. No flow was recycled to the reactor. The process was operated during 28.5 h to equilibration.

The conversion rate of glycerol and hydrogen chloride were respectively 89.2% and 67%.

The global dichloropropanol productivity estimated from the flows and the compositions of the condensate and the overflow outlet was 37.6 g dichloropropanol/h/l.

The selectivity in glycerol oligomers (i.e. diglycerol, cyclic diglycerol, monochlorohydrin and dichlorohydrin of diglycerol) was 2.0% based on the reacted glycerol.

The global concentration in the liquid mixture collected at the overflow outlet was 21 g/kg for the sum of diglycerol, cyclic diglycerol, monochlorohydrin and dichlorohydrin of diglycerol and heavy products not quantified in the gas chromatography (GC) analysis. The concentration of heavy products not quantified in the GC analysis in g/kg is estimated by difference between 1000 and the sum of the concentrations of HCl, water and the identified products in the GC analysis (adipic acid, glycerol, glycerol monochlorohydrin, glycerol dichlorohydrin and esters of glycerol, glycerol monochlorohydrin and glycerol dichlorohydrin).

EXAMPLE 2

Not According to the Invention

A mixture of glycerol and adipic acid containing 7.3% w/w adipic acid has been prepared by addition of adipic acid to glycerin containing 0.5 g/kg of diglycerol and 23 g/kg of cyclic diglycerol. Aqueous hydrochloric acid with a concentration of 5.8 mol of hydrogen chloride/kg of solution and the mixture of glycerol and adipic acid have been introduced at a constant flow rate of respectively 88.7 g/h and 25.9 g/h into a 350 ml glass reactor thermostatted at a temperature of 120° C. The reactor, which functioned at atmospheric pressure, was equipped with an overflow system for maintaining a constant volume of liquid. The reaction mixture fraction that was vaporized was evacuated from the reactor and condensed at ambient temperature. The condensate is a homogeneous aqueous phase containing most of the hydrochloric acid which had not reacted and a part of the dichloropropanol production. The liquid mixture collected at the overflow outlet contained the remainder of the dichloropropanol production. No flow was recycled to the reactor. The process was operated during 33 h to equilibration.

The conversion rate of glycerol and hydrogen chloride were respectively 88.1% and 66%.

The global dichloropropanol productivity estimated from the flows and the compositions of the condensate and the overflow outlet was 35.4 g dichloropropanol/h/l.

The selectivity in the production of oligomers (i.e. diglycerol, cyclic diglycerol, monochlorohydrin and dichlorohydrin of diglycerol) was 1.9% based on the reacted glycerol.

The global concentration in the liquid mixture collected at the overflow outlet was 61 g/kg for the sum of diglycerol, cyclic diglycerol, monochlorohydrin and dichlorohydrin of diglycerol and heavy products not quantified in the GC analysis.

The invention claimed is:

1. A process for manufacturing dichloropropanol, wherein a composition comprising:
   glycerol in an amount greater than or equal to 500 g of glycerol per kg of composition, and
   at least one cyclic dimer of glycerol in an amount of 0.01 g to 20 g of cyclic dimer per kg of composition is reacted with a chlorinating agent to produce dichloropropanol.

2. The method according to claim 1, wherein said composition further comprises at least one glycerol dimer selected from the group consisting of glycerol dimers of linear structure, non cyclic glycerol dimers of branched structure, and mixtures thereof.

3. The process according to claim 1, further comprising subjecting the dichloropropanol to a dehydrochlorination reaction to produce epichlorohydrin.

4. The process according to claim 3, wherein the epichlorohydrin is further subjected to a reaction with at least one compound selected from the group consisting of monoalcohols, monocarboxylic acids, polyols, polyamines, amino alcohols, polyimides, polyamides, polycarboxylic acids, ammonia, amines, polyaminoamides, polyimines, amine salts, phosphoric acid, phosphoric acid salts, phosphorus oxychlorides, phosphoric acid esters, phosphonic acids, esters of phosphonic acids, salts of phosphonic acids, phosphinic acids, esters of phosphinic acids, salts of phosphinic acids, phosphine oxides, phosphines, ethoxylated alcohols, alkylene oxides, phenylene oxides, and mixtures of at least two of these compounds, or
   wherein the epichlorohydrin is further subjected to a homopolymerization reaction, or
   wherein the epichlorohydrin is further subjected to a reaction selected from the group consisting of oligomerisation, co-oligomerisation, condensation, dehydrochlorination, and hydrolysis, with water, or with a di- or polyhydroxylated compound which optionally is halogenated and/or optionally has ether oxide bonds and/or double bonds capable of being halogenated in a subsequent stage, or
   wherein the epichlorohydrin is further subjected to a reaction with water,
   in order to manufacture epoxy resins or glycidyl ethers or glycidyl esters or glycidyl amides or glycidyl imides or glycidyl amines or products that can be used as coagulants or water-resistant resins or cationization agents or flame retardants or ingredients for detergents or epichlorohydrin elastomers or halogenated polyethers-polyols or monochloropropanediol.

5. The process according to claim 1, wherein said at least one cyclic dimer of glycerol is selected from the group consisting of cis- and trans-2,5-bis-(hydroxymethyl)-1,4-dioxane, cis- and trans-2,6-bis(hydroxymethyl)-1,4-dioxane, cis- and trans-6-hydroxy-2-hydroxymethyl-1,4-dioxepane, cis- and trans-3,7-dihydroxy-1,5-dioxocane, and any mixture thereof.

6. The process according to claim 1, wherein said composition comprises glycerol in an amount greater than or equal to 950 g of glycerol per kg of composition.

7. The process according to claim 1, wherein said composition comprises glycerol in an amount greater than or equal to 999 g of glycerol per kg of composition.

8. The process according to claim 1, wherein said composition comprises glycerol in an amount greater than or equal to 999.9 g of glycerol per kg of composition.

9. The process according to claim 5, wherein said composition comprises glycerol in an amount greater than or equal to 999 g of glycerol per kg of composition.

10. The process according to claim 5, wherein said composition comprises glycerol in an amount greater than or equal to 999.9 g of glycerol per kg of composition.

11. The process according to claim 1, wherein said composition comprises said at least one cyclic dimer of glycerol in an amount of 0.05 g to 10 g of cyclic dimer per kg of composition.

12. The process according to claim 1, wherein said composition comprises said at least one cyclic dimer of glycerol in an amount of 0.05 g to 1 g of cyclic dimer per kg of composition.

13. The process according to claim 7, wherein said composition comprises said at least one cyclic dimer of glycerol in an amount of 0.05 g to 10 g of cyclic dimer per kg of composition.

14. The process according to claim 7, wherein said composition comprises said at least one cyclic dimer of glycerol in an amount of 0.05 g to 1 g of cyclic dimer per kg of composition.

15. The process according to claim 5, wherein said composition comprises glycerol in an amount greater than or equal to 950 g of glycerol per kg of composition.

* * * * *